(12) United States Patent
Garini et al.

(10) Patent No.: US 9,885,705 B2
(45) Date of Patent: Feb. 6, 2018

(54) CELL ANALYSIS USING DYNAMIC BIOPHYSICAL METHODS

(71) Applicant: Bar-Ilan University, Ramat Gan (IL)

(72) Inventors: Yuval Garini, D.N. Misgav (IL); Irena Bronshtein Berger, Jerusalem (IL); Eldad Kepten, D.N. Misgav (IL)

(73) Assignee: BAR-ILAN UNIVERSITY, Ramat Gan (IL)

( * ) Notice: Subject to any disclaimer, the term of this patent is extended or adjusted under 35 U.S.C. 154(b) by 116 days.

(21) Appl. No.: 15/044,207

(22) Filed: Feb. 16, 2016

(65) Prior Publication Data

US 2016/0238610 A1 Aug. 18, 2016

(30) Foreign Application Priority Data

Feb. 16, 2015 (GB) .................................. 1502579.4

(51) Int. Cl.
| | | |
|---|---|---|
| *G01N 33/50* | (2006.01) | |
| *G01N 15/14* | (2006.01) | |
| *G01N 21/64* | (2006.01) | |
| *G01N 15/10* | (2006.01) | |

(52) U.S. Cl.
CPC ..... *G01N 33/5029* (2013.01); *G01N 15/1427* (2013.01); *G01N 15/1429* (2013.01); *G01N 15/1475* (2013.01); *G01N 21/6408* (2013.01); *G01N 21/6458* (2013.01); *G01N 2015/1006* (2013.01); *G01N 2015/1488* (2013.01); *G01N 2333/4712* (2013.01); *G01N 2333/66* (2013.01); *G01N 2333/78* (2013.01)

(58) Field of Classification Search
CPC ........... G01N 33/5029; G01N 15/1427; G01N 15/1429; G01N 15/1475; G01N 21/6408; G01N 21/6458; G01N 2015/1006; G01N 2015/1488; G01N 2333/4712; G01N 2333/66; G01N 2333/78
See application file for complete search history.

(56) References Cited

U.S. PATENT DOCUMENTS 5,149,972 A * 9/1992 Fay ..................... G01N 21/6458
250/372
5,784,162 A * 7/1998 Cabib ................... C12Q 1/6841
250/461.2
(Continued)

FOREIGN PATENT DOCUMENTS

WO 20060017942 A1 2/2006

OTHER PUBLICATIONS

Wachsmuth et al., Biophysical Journal, May 2003, "Analyzing Intracellular Binding and Diffusion with Continuous Fluorescence Photobleaching", pp. 3353-3363.*
(Continued)

*Primary Examiner* — Manav Seth
(74) *Attorney, Agent, or Firm* — The Roy Gross Law Firm, LLC; Roy Gross

(57) ABSTRACT

A method for identifying the expression or activity of a nuclear protein in a cell, the method comprising: analyzing multiple images of one or more labeled genetic entities; determining from said analysis, a motile property of said one or more labeled genetic entities; and identifying an expression or activity of a nuclear protein of said cell associated with said motile property.

9 Claims, 18 Drawing Sheets

(56) References Cited

U.S. PATENT DOCUMENTS

| | | | | | |
|---|---|---|---|---|---|
| 6,221,592 | B1* | 4/2001 | Schwartz | ............ | C12Q 1/6869 435/6.11 |
| 6,607,888 | B2* | 8/2003 | Schwartz | ............ | C12Q 1/6869 435/6.14 |
| 7,557,915 | B2* | 7/2009 | Maier | ............ | G01J 3/28 356/301 |
| 7,907,769 | B2* | 3/2011 | Sammak | ............ | G06K 9/00127 382/133 |
| 8,189,900 | B2* | 5/2012 | Sammak | ............ | G06K 9/00127 382/133 |
| 8,809,809 | B1* | 8/2014 | Wu | ............ | G02B 21/16 250/458.1 |
| 9,117,273 | B2* | 8/2015 | Sibarita | ............ | G02B 21/0076 |
| 2002/0061523 | A1* | 5/2002 | Schwartz | ............ | C12Q 1/6869 435/6.14 |
| 2008/0274905 | A1* | 11/2008 | Greene | ............ | G01N 21/6428 506/4 |
| 2009/0290780 | A1* | 11/2009 | Kottig | ............ | G01N 21/6408 382/133 |
| 2013/0294645 | A1* | 11/2013 | Sibarita | ............ | G02B 21/0076 382/103 |

OTHER PUBLICATIONS

Ries, J. et al., "Fluorescence correlation spectroscopy", BioEssays, May 2012, pp. 361-368, vol. 34, issue 5, Wiley Periodicals.

Bronshtein Berger, I. et al., "Single-Particle Tracking for Studying the Dynamic Properties of Genomic Regions in Live Cells", Imaging Gene Expression—Methods and Protocols, Part II, 2013, pp. 139-151, vol. 1042, Humana Press.

Day, R. N., et al., "The fluorescent protein palette: tools for cellular imaging", Chemical Society Reviews, Aug. 2009, pp. 2887-2921, vol. 38.

Kepten, E. et al., "Improved estimation of anomalous diffusion exponents in single-particle tracking experiments", Physical Review E, May 20, 2013., pp. 052713-, vol. 87, Issue: 5, American Physical Society.

Shav-Tal, Y. et al., "Dynamics of Single mRNPs in Nuclei of Living Cells", Science, Jun. 18, 2004, pp. 1797-1800, vol. 304, Issue: 5678.

Stixova, L. et al., "Trajectories and nuclear arrangement of PML bodies are influenced by A-type lamin deficiency", Biology of the Cell, Jul. 2012, pp. 418-432, vol. 104, Issue: 7.

Wachsmuth et al., Genome organization: Balancing stability and plasticity. Biochimica et Biophysica Acta, 2008. 1783: p. 2061-2079.

Yildiz, A., et al., Myosin V walks hand-over-hand: single fluorophore imaging with 1.5-nm localization, Science, 2003. 300: p. 2061-2066.

Bronstein, I., et al., Transient anomalous diffusion of telomeres in the nucleus of mammalian cells, Physical Review Letters, 2009. 103: p. 018102.

Franco Preparata & S.J. Hong, "Convex Hulls of Finite Sets of Points in Two and Three Dimensions", Communications of the ACM 20, 87-93 (1977).

Christian P Bacher et al., "4-D single particle tracking of synthetic and proteinaceous microspheres reveals preferential movement of nuclear particles along chromatin—poor tracks", BMC Cell Biology, p. 1-14, 2004.

Thorsten Kues et al., "Visualization and Tracking of Single Protein Molecules in the Cell Nucleus", Biophysical Journal, vol. 80, p. 2954-2967, 2001.

Valeria Levi et al., "Chromatin Dynamics in Interphase Cells Revealed by Tracking in a Two-Photon Excitation Microscope", Biophysical Journal, vol. 89, p. 4275-4285, 2005.

* cited by examiner

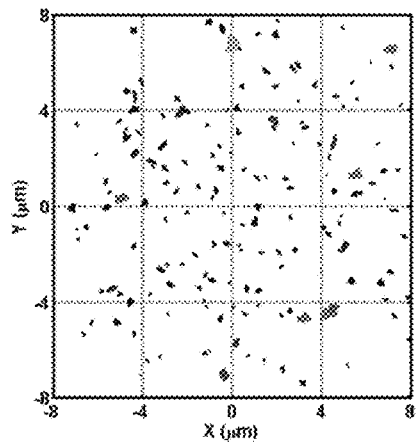
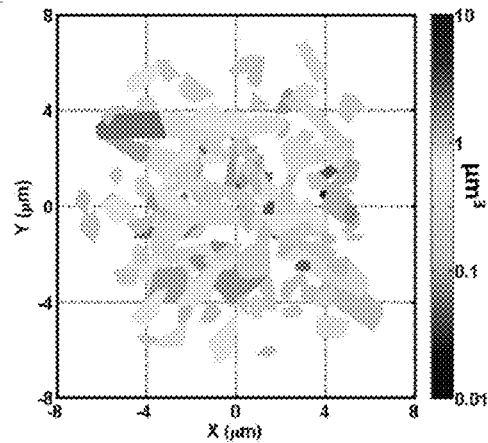
FIG. 8A    FIG. 8B
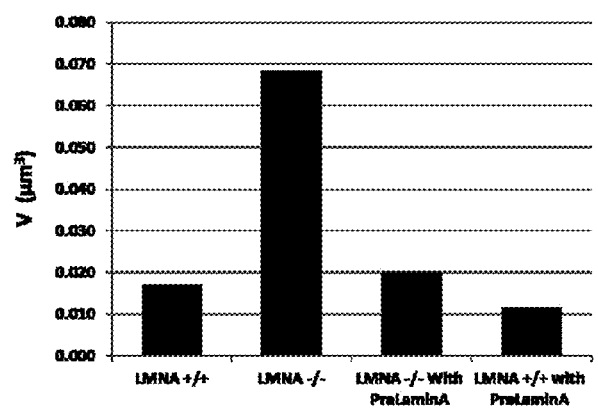
FIG. 8C

CELL ANALYSIS USING DYNAMIC BIOPHYSICAL METHODS

RELATED APPLICATION/S

This application claims the benefit of priority of GB Patent Application No. 1502579.4 filed Feb. 16, 2015, the contents of which are incorporated herein by reference in their entirety.

FIELD OF THE INVENTION

The invention relates to the field of cell analysis.

BACKGROUND

It is common to divide dynamic processes in live cells to one of three categories: diffusion of free or partly free proteins and inter-cellular entities; binding and unbinding of proteins to different inter-cellular entities; and structural changes to all or part of the cell. In general, each one of these categories describes a process that occurs in a different time scale, such as described in Wachsmuth et al., *Genome organization: Balancing stability and plasticity*. Biochimica et Biophysica Acta, 2008. 1783: p. 2061-2079.

Unbound molecules, such as a freely diffusing protein in a cell may travel a distance of micrometer in a fraction of a millisecond, whereas binding and unbinding of proteins may occur over a time range of between a millisecond to several seconds, and changes to cell structure typically happen over a time range of minutes to hours. Below we describe few of the most relevant methods for measuring the above-described processes in live cells. These methods, with very few exceptions, require labeling the studied proteins or structures with fluorescent dyes. Such methods are well developed through inserted fluorescent molecules, or through transfection of the cells with the DNA transcripts of fluorescent proteins that expresses the fluorescent proteins in the live cells.

Fluorescence correlation spectroscopy (FCS) is one common method for measuring motion of molecules while they bounce in and out of a small, defined region in a cell, as described in Ries, J. and P. Schwille, *Fluorescence correlation spectroscopy*. Bioassays, 2012. 34: p. 361-368. An entity, such as a molecule, may be labeled with a fluorescent dye and measured via fluorescence microscopy, where the size of an illuminated spot may be bound by the optics of the microscope used to measure it, and which may be limited by the point spread function of the microscope optics. The intensity of the illuminated spot may fluctuate and an autocorrelation function of the intensity may be calculated. The typical time that a particle remains within the small spot under measurement may correspond to the typical time that the autocorrelation function reduces to zero. This method may be applicable for measuring freely diffusing entities in the cell, where the diffusion coefficients are usually in the range of $1\text{-}100\times10^{-4}$ $\mu m^2/sec$. Although FCS may also be used for measuring binding processes, it may become complex and the extracted data may depend on the model that is being used for the analysis.

Another relevant method for measuring entity motion within a cell is fluorescence recovery after photobleaching (FRAP). In this method, both the diffusion and the binding properties of a selected protein may be measured. This method typically requires labeling the protein with a fluorescent dye. A sample of one or more cells may be initially measured. A high-intensity laser may then mark, or 'burn' the fluorescing molecules within a defined region in a technique also known as 'bleaching'. The cellular sample may be repeatedly measured. If the sample in the bleached area recovers, one may extrapolate the typical time it takes the molecules to be replaced within the bleached area.

Continuous photobleaching (CP) is third method for measuring the motion of inter-cellular entities, and is typically simpler than FRAP.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a method for identifying the expression or activity of a protein in a cell, the method comprising using at least one hardware processor for: analyzing multiple images of one or more labeled genetic entities; determining from said analysis, a motile property of said one or more labeled genetic entities; and identifying an expression or activity of a protein of said cell associated with said motile property.

There is further provided, in accordance with an embodiment, a computer program product for determining a cell characteristic, the computer program product comprising a non-transitory computer-readable storage medium having program code embodied therewith, the program code executable by at least one hardware processor to: analyze multiple images of one or more labeled genetic entities; determine from said analysis, a motile property of said one or more labeled genetic entities; and identify an expression or activity of a nuclear protein of said cell associated with said motile property.

There is provided, in accordance with an embodiment, a system for determining a cell characteristic, the system comprising: a microscope configured to magnify one or more labeled genetic entities; a camera configured to capture multiple images of said one or more labeled genetic entities, wherein said camera is coupled to said microscope; and a processor configured to analyze said multiple images; determine from said analysis, a motile property of said one or more labeled genetic entities; and identify an expression or activity of a nuclear protein of said cell associated with said motile property.

There is further provided, in accordance with an embodiment, a system for determining a cell characteristic, the system comprising: a camera configured to capture multiple images of one or more labeled genetic entities; and a processor configured to analyze said multiple images; determine from said analysis, a motile property of said one or more labeled genetic entities; and identify an expression or activity of a protein of said cell associated with said motile property.

There is provided, in accordance with an embodiment, an apparatus for determining a cell characteristic, the apparatus comprising: a processor configured to analyze multiple images of one or more labeled intra-nuclear genetic entities; determine from said analysis, a motile property of said one or more labeled intra-nuclear genetic entities; and identify an expression or activity of a nuclear protein of said cell associated with said motile property.

In some embodiments, said camera comprises a charged coupled device or a confocal microscope. In some embodiments, said processor is further configured to analyze said captured images by eliminating a rotational and/or translational movement attributed to a nucleus of said cell. In some embodiments, said images are captured via a camera comprising a charged coupled device or a confocal microscope. In some embodiments, said processor is further configured to identify by applying a rule to said space function.

In some embodiments, said genetic entities are selected from the group consisting of: telomeres, centromeres, a specific gene locus, nuclear bodies, a nucleolus, and one or more proteins bound thereto.

In some embodiments, said labeling comprises fluorescently labeling. In some embodiments, said labeled genetic entities are fluorescently labeled.

In some embodiments, said protein comprises a structural nuclear protein. In some embodiments, said protein is different than said genetic entity. In some embodiments, said protein is selected from the group consisting of Lamin A, Lamin B, Lamin C, Lap2α, Lap2-beta, BAF, actin and emerin.

In some embodiments, analyzing said captured images further comprises eliminating a rotational and/or translational movement attributed to a nucleus of said cell.

In some embodiments, said images are captured via a charged coupled device or via using confocal microscopy.

In some embodiments, said motile property comprises a diffusion characteristic of said labeled genetic entities.

In some embodiments, determining said diffusion characteristic comprises calculating a space function with respect to time. In some embodiments, said space function is derived from multiple path trajectories calculated from said multiple images of said one or more labeled genetic entities. In some embodiments, said space function is a mean square distance (MSD) function. In some embodiments, the space function is a mean square volume (MSV) function.

In some embodiments, said space function represents a space spanned by said labeled genetic entities. In some embodiments, said space function represents a space scanned by said labeled genetic entities.

In some embodiments, said space function comprises a two-dimensional area function. In some embodiments, said space function comprises a three-dimensional volume function.

In some embodiments, said identifying comprises applying a rule to said space function. In some embodiments, said rule associates a linear property of said space function with a normal diffusion characteristic for said labeled genetic entities and a depletion of a concentration of said protein. In some embodiments, said rule associates a logarithmic property of said space function with an anomalous sub diffusion characteristic for said labeled genetic entities and a normal concentration of said protein. In some embodiments, said rule comprises associating an exponentially increasing property of said space function with an anomalous subdiffusion or superdiffusion characteristic for said protein. In some embodiments, said rule comprises associating a linear property of said space function for a first time period and a logarithmic property of said space function for a second time period with a normal diffusion characteristic for said labeled genetic entities within a restricted volume of said cell.

There is provided, in accordance with an embodiment, a method for determining the ratio of bound to unbound molecules in a cell, comprising: obtaining, from a selected area of a cell, data comprising time-resolved emitted light intensity measurements and time-resolved fluorescent lifetime measurements of fluorescently labeled bound molecules and fluorescently labeled unbound molecules; determining from the obtained data 1) a continuous photobleaching (CP) curve and 2) fluorescent lifetime histograms for each of the time-resolved emitted light intensity measurements and fluorescent lifetime measurements; and calculating a ratio of the fluorescently labeled bound molecules to the fluorescently labeled unbound molecules in the selected regions using the CP curve and the fluorescent lifetime histograms.

In some embodiments, the method further comprises fluorescently labeling the molecules; selecting the area; illuminating the selected area with light corresponding to the molecules' absorption spectrum; detecting the light intensity emitted from the illuminated area; and measuring the fluorescent lifetimes of the bound molecules to the unbound molecules.

In some embodiments, the method further comprises synchronizing the illumination and detection steps.

In some embodiments, synchronizing comprises applying any of a gating technique, time correlated single photon counting technique, and phase modulation technique.

In some embodiments, calculating further comprises correlating the CP curve with the fluorescent lifetime histograms over time.

In some embodiments, illuminating comprises emitting a laser pulse having a duration ranging between 1 and 1000 picoseconds.

In some embodiments, the molecules are fluorescently labeled using fluorescing molecules selected from the group consisting of molecular probes, fluorescent proteins, quantum dots, metallic particles, and a dye measurable via bright field microscopy.

In some embodiments, the measuring step is performed using any of: a fluorescent microscope, a transmission microscope, a dark-field microscopy apparatus, a confocal microscope, a total internal reflection microscopy apparatus, a super resolution microscopy apparatus, and a fluorescence life-time microscopy apparatus.

In some embodiments, the measuring step comprises determining any of the fluorescent light intensity and an emitted photon count per a predetermined time unit.

In some embodiments, the method further comprises repeating performing said obtaining, determining and calculating steps for a time window ranging from one millisecond to one hundred seconds.

In some embodiments, measuring the light intensity comprises optically filtering the spectral range of the excitation spectral band from the emission spectral band of the emitted light.

In some embodiments, the method further comprises rendering the calculated ratio of bound molecules to unbound molecules on a user interface.

There is provided, in accordance with an embodiment, a system for determining the ratio of bound to unbound molecules in a cell, comprising: a processor configured to: obtain, from a selected area of a cell, data comprising time-resolved emitted light intensity measurements and time-resolved fluorescent lifetime measurements of fluorescently labeled bound molecules and fluorescently labeled unbound molecules; determining from the obtained data 1) a continuous photobleaching (CP) curve and 2) fluorescent lifetime histograms for each of the time-resolved emitted light intensity measurements and fluorescent lifetime measurements; and calculate a ratio of the fluorescently labeled bound molecules to the fluorescently labeled unbound molecules in the selected area using the CP curve and the fluorescent lifetime histograms.

In some embodiments, the processor is further configured to correlate the CP curve with the fluorescent lifetime histograms over time.

In some embodiments, the light source comprises a pulsed picosecond diode laser configured to emit a pulse having a duration ranging between 1 and 1000 picoseconds.

In some embodiments, the molecules are fluorescently labeled using fluorescing molecules selected from the group consisting of molecular probes, fluorescent proteins, quantum dots, metallic particles, and a dye measurable via bright field microscopy.

In some embodiments, the system further comprises: a light source configured to illuminate the selected region with light corresponding to the molecules' absorption spectrum; and a microscope configured to detect the light intensity emitted from the illuminated molecule.

In some embodiments, the microscope comprises any of an avalanche photodiode, a single photon avalanche detector, and a hybrid detector.

In some embodiments, the microscope comprises any of: a fluorescent microscope, a transmission microscope, a dark-field microscopy apparatus, a confocal microscope, a total internal reflection microscopy apparatus, a super resolution microscopy apparatus, and a fluorescence life-time microscopy apparatus.

In some embodiments, the system further comprises an electronic counter configured to synchronize the illumination by the light source with the measuring by the microscope, thereby measuring the fluorescent lifetimes of the bound molecules to the unbound molecules.

In some embodiments, synchronizing comprises applying any of a gating technique, time correlated single photon counting technique, and phase modulation technique.

In some embodiments, the electronic synchronizer is configured to measure a time duration ranging from 0.5 picoseconds to multiple seconds.

In some embodiments, the microscope is configured to measure any of the fluorescent light intensity and an emitted photon count per a predetermined time unit.

In some embodiments, the system further comprises an optical filter configured to filter the spectral range of the excitation spectral band from the emission spectral band of the emitted light.

In some embodiments, the system further comprises a light separator configured to separate the polarization of the excitation light from the polarization of the fluorescent light.

In some embodiments, the system further comprises a user interface configured to render the calculated ratio of bound molecules to unbound molecules.

There is provided, in accordance with an embodiment, a computer program product for determining a cell characteristic, the computer program product comprising a non-transitory computer-readable storage medium having program code embodied therewith, the program code executable by at least one hardware processor to: obtain, from a selected area of a cell, data comprising time-resolved emitted light intensity measurements and time-resolved fluorescent lifetime measurements of time-resolved fluorescent lifetime measurements of fluorescently bound molecules and time-resolved fluorescent lifetime measurements of fluorescently unbound molecules; determine from the obtained data 1) a continuous photobleaching (CP) curve and 2) fluorescent lifetime histograms for each of the time-resolved emitted light intensity measurements and fluorescent lifetime measurements; calculate a ratio of the time-resolved fluorescent lifetime measurements of fluorescently bound molecules to the time-resolved fluorescent lifetime measurements of fluorescently unbound molecules in the selected area using the CP curve and the fluorescent lifetime histograms.

In some embodiments, calculating comprises correlating the CP curve with the fluorescent lifetime histograms over time.

In some embodiments, illuminating comprises emitting a laser pulse having a duration ranging between 1 and 1000 picoseconds.

In some embodiments, the molecules are fluorescently labeled using fluorescing molecules selected from the group consisting of molecular probes, fluorescent proteins, quantum dots, metallic particles, and a dye measurable via bright field microscopy.

In some embodiments, the measuring step is performed using any of: a fluorescent microscope, a transmission microscope, a dark-field microscopy apparatus, a confocal microscope, a total internal reflection microscopy apparatus, a super resolution microscopy apparatus, and a fluorescence life-time microscopy apparatus.

In some embodiments, the time-resolved emitted light intensity measurements comprise an emitted photon count per a predetermined time unit.

In some embodiments, the program code is further executable to repeat performing said obtaining, determining and calculating steps for a time window ranging from one millisecond to one hundred seconds.

In some embodiments, the program code is further executable to render the ratio of bound molecules to unbound molecules on a user interface.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 1I shows a distribution for a population whose ratio of short lifetime sub-population to long lifetime sub-population is approximately 80%, FIG. 1J shows a distribution for a population whose ratio of short lifetime sub-population to long lifetime sub-population ranges from approximately 20%-40%, and FIG. 1K shows a distribution for a population whose ratio of short lifetime sub-population to long lifetime sub-population is approximately 5%-10%;

FIGS. 8A-8C, taken together, show experimental results of an area scanned by 350 randomly selected telomeres during 15 minutes as calculated using a convex hull algorithm, in accordance with an embodiment of the invention. Data is shown for two cell types;

DETAILED DESCRIPTION

Figure 1A:
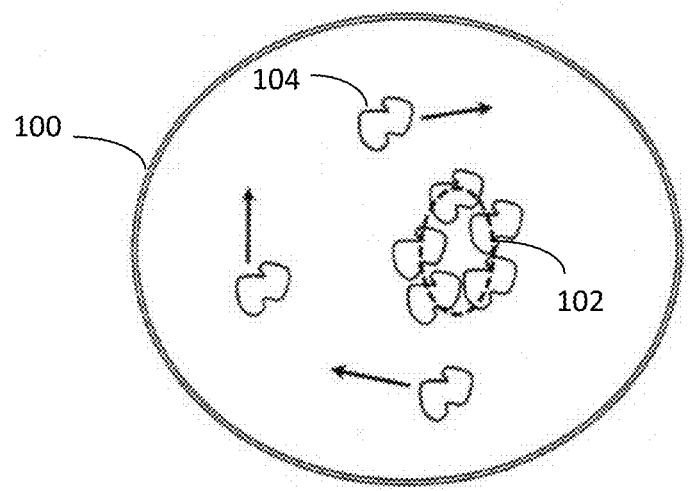
FIG. 1A shows a schematic diagram of a biological entity having a bound subpopulation (indicated by the inner dashed circle) and a freely diffusing subpopulation.

A system and method is disclosed herein to identify an expression or activity of a protein in a cell by analyzing multiple images of labeled genetic entities over time using the techniques disclosed herein, and determining a motile property, such as diffusion characteristic of the genetic entities.

In general, dynamic processes in live cells may be categorized in several ways: a) as diffusion of free or partly free proteins and entities, b) as binding and unbinding of proteins to different subcellular entities, and c) as structural changes to part or all of the cell, where each process type occurs over a different time scale. For example, a freely diffusing protein in a cell may travel over a distance of a micrometer in a fraction of a millisecond, proteins may bind and unbind over a time duration ranging from several milliseconds to a few seconds, and cellular structural changes transpire over a time duration ranging from several minutes to hours (a cell typically divides in about 20 hours). Due to the large range of time durations, different measuring techniques may be used for these categories.

In one embodiment, a method is disclosed to identify the type of dynamic process by imaging specific labeled proteins in a live cell and analyzing the images. The fluorescent lifetime of fluorescently labeled proteins expressed in cells are measured, and the variations in intensity are tracked over time. Since the fluorescent lifetime is dependent on the state of the protein, such as if it is bound or free, the combination of the intensity as a function of time with the lifetime information may allow determining the ratio of bound to free proteins in the cell.

In another embodiment, the diffusion characteristic may be determined by calculating a function of space that is covered by the labeled genetic entities over time, and that may be derived from multiple path trajectories determined from the multiple images. The space function may comprise a two-dimensional area function, or alternatively, a three-dimensional volume function.

One or more rules may be applied to the space function to associate a property, such as the shape or derivative of the space function, with a diffusion characteristic corresponding to an expression of the protein that may characterize the cell. For example, a linear property of the function may be associated with a normal diffusion for the labeled entities, a logarithmic property of the function may be associated with an anomalous subdiffusion for the labeled entities, and an exponential property of the function may be associated with an anomalous subdiffusion or superdiffusion for the labeled entities. Additionally, a linear property of the function for a first time period and a logarithmic property of the function for a second time period may be associated with a normal diffusion characteristic for the labeled entities within a restricted volume of the cell. A more detailed discussion associating these diffusion types with the cell characteristic is given below.

Without limiting the present invention to any particular theory, an analysis of the diffusion properties of intranuclear genetic entities may determine the presence or depletion of one or more nuclear proteins that may indicate a genetic abnormality, or phenotype of a disease, such as cancer, de novo syndrome, and/or an inherited disease such as muscular dystrophy.

As used herein, the term "genetic entities" refers to a chromosomal region that can be specifically labeled, such as telomeres, centromeres, a specific gene locus, nuclear bodies such as a promyelocytic leukemia protein (PML), the nucleolus, and/or any proteins or nucleic acid molecule bound thereto. These genetic entities may be labeled using any suitable means, such as via a fluorescent probe including any of molecular probes, fluorescent proteins, quantum dots, metallic particles, or a dye which, in some embodiments, can be measured with a light or bright field microscope.

In one embodiment, the determined diffusion characteristics of labeled genetic entities may be applied to determine the expression, activity, depletion and/or concentration levels of any of the nuclear or structural nuclear proteins, including but not limited to: Lamin A, Lamin B, Lamin C, lamina-associated polypeptide-2 (Lap2)α, Lap2-beta, barrier-to-autointegration factor (BAF), actin, or emerin.

In some embodiments, said nuclear proteins are inner nuclear membrane (INM) proteins such as Lap1, Lap2, lamin B receptor (LBR), emerin, and LEM domain-containing protein 3 (LEMD3; also known as MAN1).

In one embodiment, the invention provides methods for identifying the expression, activity, depletion and/or concentration levels of a lamin protein such as lamin A. In some embodiments, the methods of the inventions are useful for diagnosing laminopathy or nuclear envelopathies in a subject in need thereof, or whether said subject is at risk at developing laminopathy or nuclear envelopathies. Laminopathies and other nuclear envelopathies are known in the art and include Atypical Werner syndrome, Barraquer-Simons syndrome, Buschke-Ollendorff syndrome, Cardiomyopathy, Charcot-Marie-Tooth disease, Emery-Dreifuss muscular dystrophy, Familial partial lipodystrophy of the Dunnigan type (FPLD), Greenberg dysplasia, Hutchinson-Gilford progeria syndrome (HGPS), Leukodystrophy, Limb-girdle muscular dystrophy type 1B (LGMD1B), Lipoatrophy with diabetes, Mandibuloacral dysplasia with type A lipodystrophy (MADA), Mandibuloacral dysplasia with type B lipodystrophy (MADB), Pelger-Huet anomaly (PHA), Pelizaeus-Merzbacher disease and tight skin contracture syndrome, among others.

In another embodiment, the labeled genetic entity that is analyzed to determine a motile property therefrom, is different than the nuclear protein for which the expression or activity is identified thereto.

The term "fluorescent marker" as used herein, refers to a substance or a site thereof that is detectable by fluorescence within a detectable range. These markers include proteins or peptides that can be detected by fluorescence within or compounds that show fluorescence within a specific wavelength range. Examples of proteins used as fluorescence markers including but not limited to green fluorescent protein (GFP), modified green fluorescent protein (mGFP), enhanced green fluorescent protein (EGFP), red fluorescent protein (RFP), modified red fluorescent protein (mRFP), enhanced red fluorescent protein (ERFP), blue fluorescent protein (BFP), enhanced blue fluorescent protein (EBFP), yellow fluorescent protein (YFP), enhanced yellow fluorescent protein (EYFP), cyan fluorescent protein (CFP) and enhanced cyan fluorescentprotein (ECFP). FITC (Fluorescein isothiocyanate), TRTTC (tetramethyl-rhodamine isothiocyanate), Cy3 (Cyanine 3), Cy5 (Cyanine 5) or rhodamine may be also used as a fluorescence or UV indicator. Additional fluorescence or UV markers that can be used in the methods of the invention are well under the skill of an ordinary artisan. Other markers may include quantum dots of different sizes, normally made of elements from the 2-6 columns of the periodic table (e.g. CdTe. ZnTe) or nanometer-size metal particles that can also fluoresce.

The genetic entities (also denoted herein "particles") may be labeled by applying a fluorescent marker via a transfection procedure. For example, telomeres in the cell's nucleus may be labeled by transfecting the cell with DNA that expresses GFP-TRF2, a protein that naturally caps the telomeres, resulting in a bright and stable signal. Thus labeled, the dynamics of the marked particles within the cell may be observed and measured over a defined area and/or timeframe. The particle dynamics may be affected by one or more characters of the cell, such as the structure of the chromatin complex, which in turn may be affected by the expression of a protein within the cell. Thus, an analysis of the dynamics for one type of subcellular particle may be applied to determine the presence, concentration or effect of an indicative particle, such as a protein.

The particle dynamics may be tracked using any suitable apparatus, such by capturing images of the particles using a fluorescent microscope with an array detector such as charged coupled device (CCD) or complementary metal oxide semiconductor (CMOS) camera, or a confocal microscope with suitable illumination laser light sources and single-point detectors such as photomultiplier (PMT), avalanche photodiode (APD), hybrid detector, or any other suitable detector that can measure very low light intensity.

To measure time-intervals of $10^{-1}$-$10^2$ seconds, two-dimensional confocal microscopy at a frame-rate of 2 Hz may be applied with low photobleaching. For longer durations where nucleic motion may be significant, three-dimensional (3D) confocal microscopy may be used to capture 3D images at predefined intervals, such as every 1-100 seconds. The 3D information is important, because during a long measurement, the studied cell may move, and the 3D information can be used for correcting its motion. In both techniques, the measurement precision of the telomere spots may be estimated at approximately 5-200 nm. This may be extracted from the measurement of genomic regions in formaldehyde-fixed cells under similar measurement conditions. For faster image acquisition, a similar microscope may be used with a sensitive cooled electron multiplying CCD (EM-CCD), such as the Andor, DU-885 that can provide images at a frame rate of 1-400 images at each second.

With the CCD, a single focal plane may be selected in the cell. Typically, 10-20 telomeres may be observed on one plane, and the measurement may be captured at an image rate of 85 images per second over a duration of 20 seconds, during which the cell's movement may be insignificant, and thus the telomeres remain within the focal plane. Typically, about 50-70 telomeres may be observed when using the confocal microscope in the whole nucleus volume. The measurements may be performed using a confocal microscope or any confocal setup that allows illuminating a single point or several individual points in a selected area.

The captured images may be analyzed by a computerized hardware processor to determine the respective paths and diffusion characteristics of the labeled entities and the resulting cell characteristic. In one embodiment, the processor may be configured with the image capturing apparatus. Alternatively, the processor may obtain the image data from the image capturing apparatus using wired or wireless means.

The processor may compute entities such as: the area or volume spanned by the tracked particles in a given period, or, the mean square distance (MSD) as a function or time. The MSD function may be applied to determine one or more diffusion characteristics in accordance with one or more rules. For example, the MSD function may be compared to a set of predefined functions associated with different diffusion characteristics to determine if the particle diffusion type within the cell is normal or anomalous.

For example, Lamin A is a component of the nuclear lamina that contributes to peripheral heterochromatin association and to nuclear integrity, and may also be found in the nucleoplasm. Deficiency of lamin A may affect nucleus plasticity and chromatin dynamics leading to increased genome mobility, and may cause particle diffusion to change from slow anomalous diffusion, associated with healthy cells, to fast and normal diffusion, associated with lamin A depleted cells.

Thus, the volume or area traversed by a tracked particle in a lamin A-depleted region may be greater than the volume traversed in a region with normal levels of lamin A. By analyzing the paths travelled by tracked particles within the nucleus, levels of indicative proteins, such as lamin A, may be determined.

An analysis of the path, area, or volume traversed by a particle over time may be repeated for many particles, leading to a statistical analysis that may be used to determine a cell's genetic type.

In an embodiment, a continuous photo-bleaching method (CP) may be applied to a selected area within a cell to determine a cell characteristic, such as a motile property of a labeled protein of interest. Bleaching may affect the observed intensity level of a particle as a function of the particle's exposure to the bleaching compound: the longer the particle is exposed to the bleaching compound, the lower the observed intensity level may be for the particle. Thus, the observed intensity level of a slow-moving particle, such as a bound particle, within the bleached area may diminish substantially over an observed duration, due to its relatively long exposure to the bleaching compound. Conversely, the observed intensity level of a fast-moving particle, such as a freely diffusing or unbound particle, within the bleached area may diminish only marginally or not at all due to its short exposure to the bleaching compound. Since the nature of the observed entity determines the rate of decay of its intensity level, this property may be applied to determine the ratio of bound to unbound proteins within the cell.

Over a given time duration, the bound proteins may exhibit a high rate of bleaching due to their continued exposure to the bleaching compound, and the unbound proteins may exhibit a low rate of bleaching due to their fleeting exposure to the bleaching compound. A curve representing the measured intensity of the bleached area as a function of time may exhibit an initial exponential decay corresponding to the bleaching of any bound particles present in the area of observation, followed by a leveling off to either a constant intensity level or slow linearly decaying intensity, corresponding to the unbound particles present in the area of observation. An analysis of the decay of the intensity levels of the observed proteins may yield a ratio of bound to unbound proteins within the cell, and which may signify a characteristic of the cell such as may be used to diagnose an abnormality.

Figure 1B:
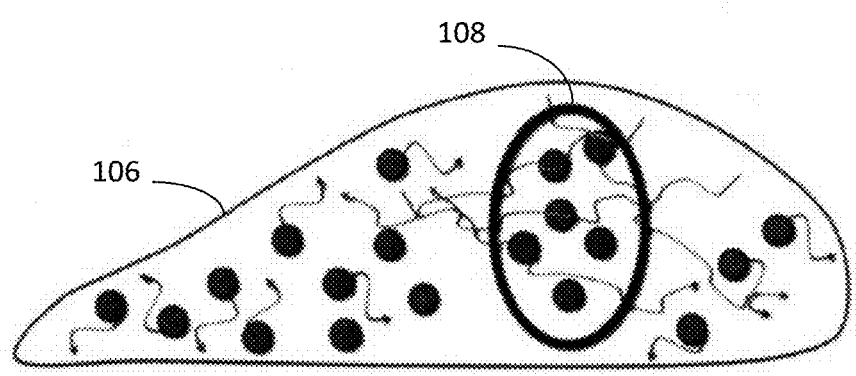
FIG. 1B shows a schematic diagram of a biological entity having free fluorescent molecules which may be bound to freely diffusing proteins within the biological entity.
Figure 1C:
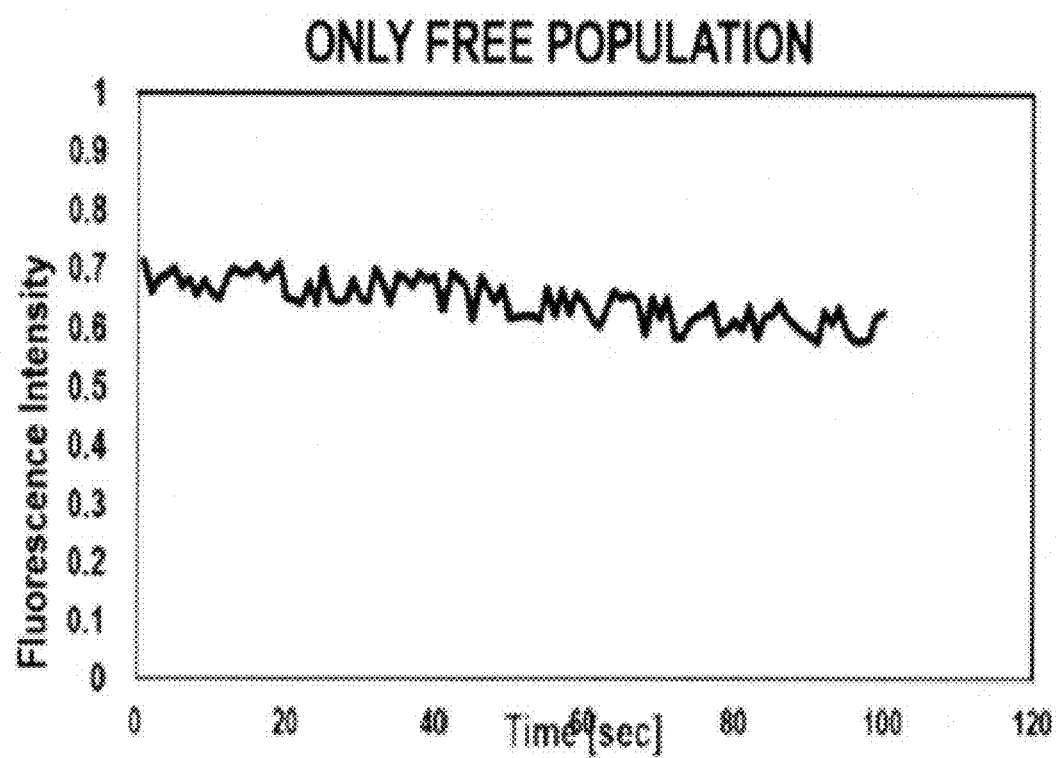
FIG. 1C shows measurements of fluorescing intensity with respect to time for a freely diffusing protein subject to continuous photobleaching (CP)

For example, referring to FIG. 1A, a conceptual illustration of a cell 100 is shown having bound entities 102 and unbound entities 104. FIG. 1B shows a conceptual illustration of a cell 106 with unbound entities diffusing through a bleached measurement area 108. FIG. 1C shows the measured intensity of the unbound entities within area 108 with respect to times. Due to the relatively fast motion of the unbound entities particles through area 108, their intensity undergoes relatively little bleaching, as indicated by the slight decay in the corresponding intensity curve of FIG. 1C.

Figure 1D:
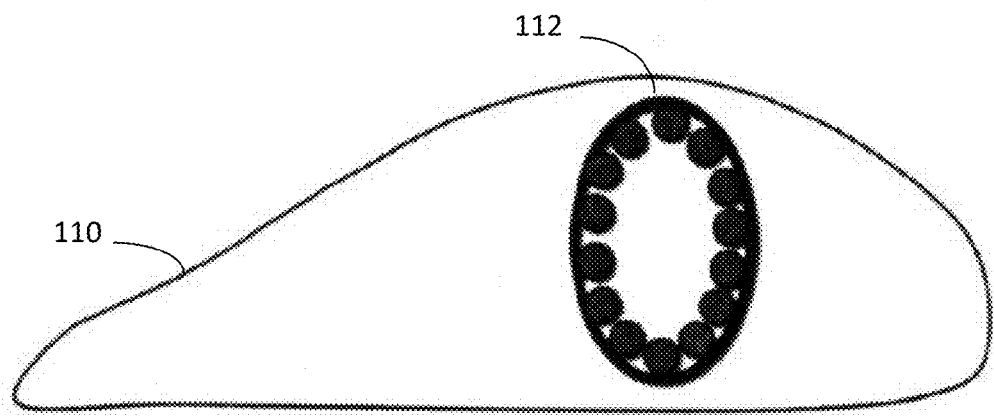
FIG. 1D shows a schematic diagram of multiple bound fluorescent molecules which may be bound to one or more proteins that are bound within a biological entity.
Figure 1E:
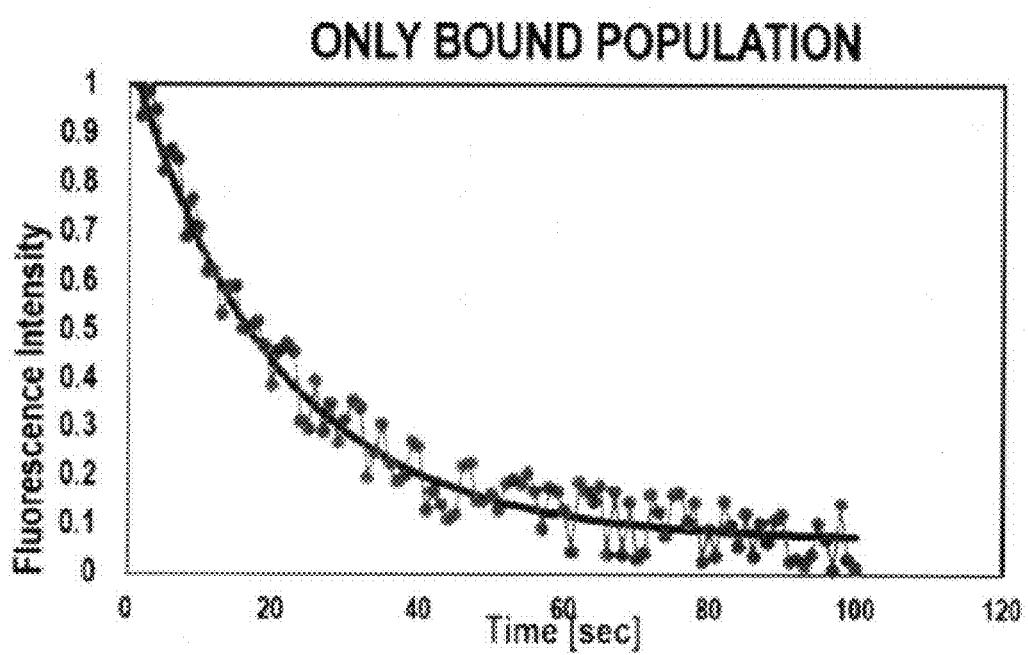
FIG. 1E shows the fluorescing intensity of a bound molecule exponentially decaying with respect to time when subject to CP.

In contrast, referring to FIGS. 1D-1E, a conceptual illustration of a cell 110 is shown having bound entities within a bleached measurement area 112. Since the bound entities remain in area 112, their intensity undergoes significant bleaching, as indicated by the marked decay of the corresponding intensity curve of FIG. 1E.

Therefore, when both bound and unbound entities are present, the corresponding intensity curve may indicate an initial exponential decay attributable to the bound entities, and a subsequent constant or slow decay attributable to the unbound entities. The ratio of the bound to unbound entities may be determined by analyzing the shape of $\tau B$ of the bound entities is large relative to the diffusion time $\tau D$ of the free entities $\tau D \ll \tau B$, the analysis may be straightforward.

Measurement may be obtained using a confocal inverted microscope, such as an Olympus, IX81 microscope and FV-1000 confocal, combined with a sensitive detection system such as a provided by a Picoquant Microtime 200 (MT200) system may be used in accordance with any of the methods disclosed herein. The MT200 system may use a 20 MHz 470 nanometer (nm) pulsed picosecond diode laser, such as a LDH-P-C-470B, 160 PicoQuant. The light may be coupled to the FV-1000 via an optical fiber and focused onto a small confocal volume through a 60× water immersion objective lens with NA=1.2 (UPIanSApo, Olympus). The emitted light may be collected through the objective, filtered from the excitation light through a dichroic mirror (405/488 nm), and transmitted through a confocal pinhole (D=120 µm) and detected with a single photon avalanche detector (SPAD-170 µm Perkin Elmer SPCM-AQRH 13) through a 520/35 nm Band-pass filter (FF01-520/35-25, Semrock Rochester N.Y., USA). This setup may be used to obtain any of the measurements described herein. Additionally or alternatively, any of fluorescent microscopy, transmission microscopy, dark-field microscopy, confocal microscopy, total internal reflection fluorescence microscopy, super resolution microscopy including any of stimulated emission depletion (STED), photoactivated localization microscopy (PALM), stochastic optical reconstruction microscopy (STORM), or structured illumination microscopy (SIM), and fluorescence life-time microscopy may be used.

The laser intensity may be initially calibrated to ~2.7 µW at the back aperture of the objective. A measurement of the cell may be performed with the confocal microscope. Then, a specific point may be chosen in the nuclear interior and a "point measurement" may be captured with the FV1000 confocal imaging set up for approximately 60 seconds. This measurement may be obtained by using the MT200 laser for excitation and SPAD detector. Additional measurements may be similarly obtained from additional cells.

The intensity of a fluorescent signal detected in a CP experiment may be proportional to the ratio of un-bleached fluorescent molecules that are still present in the optical volume. The CP data may be analyzed using any suitable method, such as via a Matlab program. The data may be smoothed, such as within a 0.1 seconds window, in an initial step. The starting point t=0 when the laser is turned on, may correspond to the maximum intensity of the time trace (FIG. 1). The observed intensity trace may be fit to a model, such as $I(t)=ae^{-bt}+ct+d$. The ratio of unbound proteins to the total volume of proteins may be calculated as the ratio between the extrapolated value for an initial linear intensity value d, corresponding to the intensity of the unbound protein volume at t=0, and the measured initial intensity value I(0), measured at t=0, and corresponding to the initial intensity value of the total volume of proteins comprising both the bound and unbound proteins.

Figure 1F:
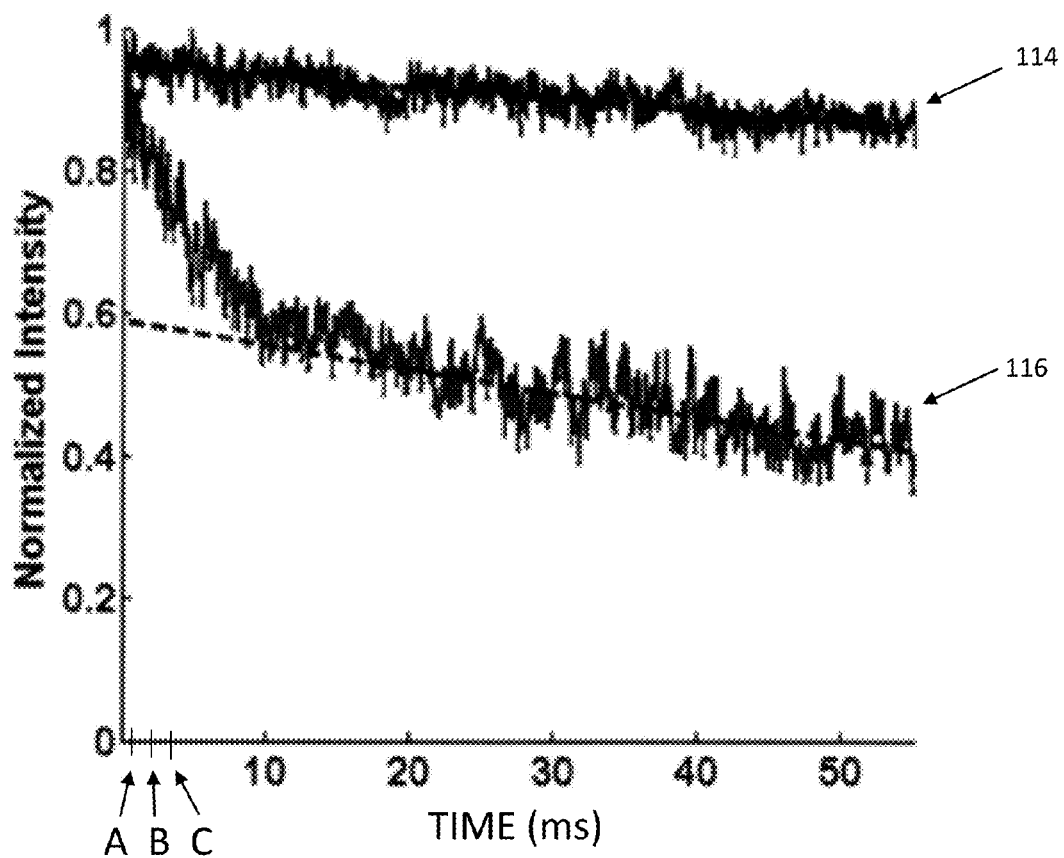
FIG. 1F shows measurements of fluorescence intensity levels with respect to time for labeled particles as measured in small regions in a cell nucleus, in accordance with an embodiment of the invention.

Reference is made to FIG. 1F, which shows CP measurements of intensity levels for labeled particles, in accordance with an embodiment of the invention. FIG. 1F illustrates measurements that were obtained for free green fluorescent protein (GFP) and for lamin A protein in a normal live cell. Curve 102 corresponds to a freely diffusing GFP in the nucleus, whereas curve 104 corresponds to fluorescently labeled Lamin A particles, and may be divided into two portions: a decaying portion for 0<t<10 seconds, and a linear portion for t>10 seconds. The linear portion of the curve may correspond to freely-diffusing particles while the decaying portion of the curve may correspond to bound particles. The proportion of free particles to the bound particles may be found by determining the ratio of the intensity of the linear fit curve (at the crossing point at t=0) and the total intensity measured at t=0. The intensity curves may be analyzed as described above. In this case, it was deduced that approximately 40% of the lamin A proteins were bound and approximately 60% were free.

τD and τB is not substantial, such as if they are within a factor of 2, 5 or even 10, the CP experiment may be performed while monitoring the fluorescent lifetime of the molecules used for the experiment.

A fluorescent molecule is excitable via illumination with light having a spectral range corresponding to the molecule's absorption spectrum. On illumination, an electron in the molecule is excited to a higher energy state where it remains until it falls back to the original state and emits a photon at a wavelength corresponding to the emission spectral band of the molecule. A typical lifetime of the excited state ranges from approximately 1-10 nanoseconds, and may exceed or fall below this range.

Figure 1G:
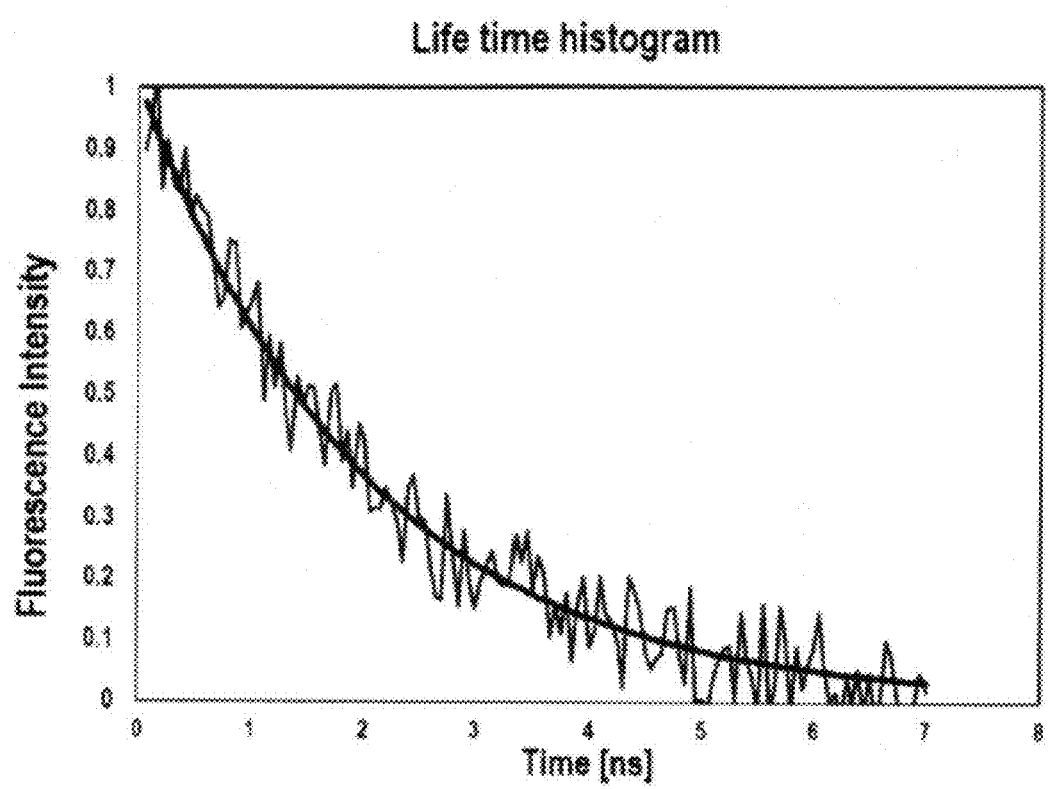
FIG. 1G shows a typical lifetime histogram for a fluorescent molecule.
Figure 1H:
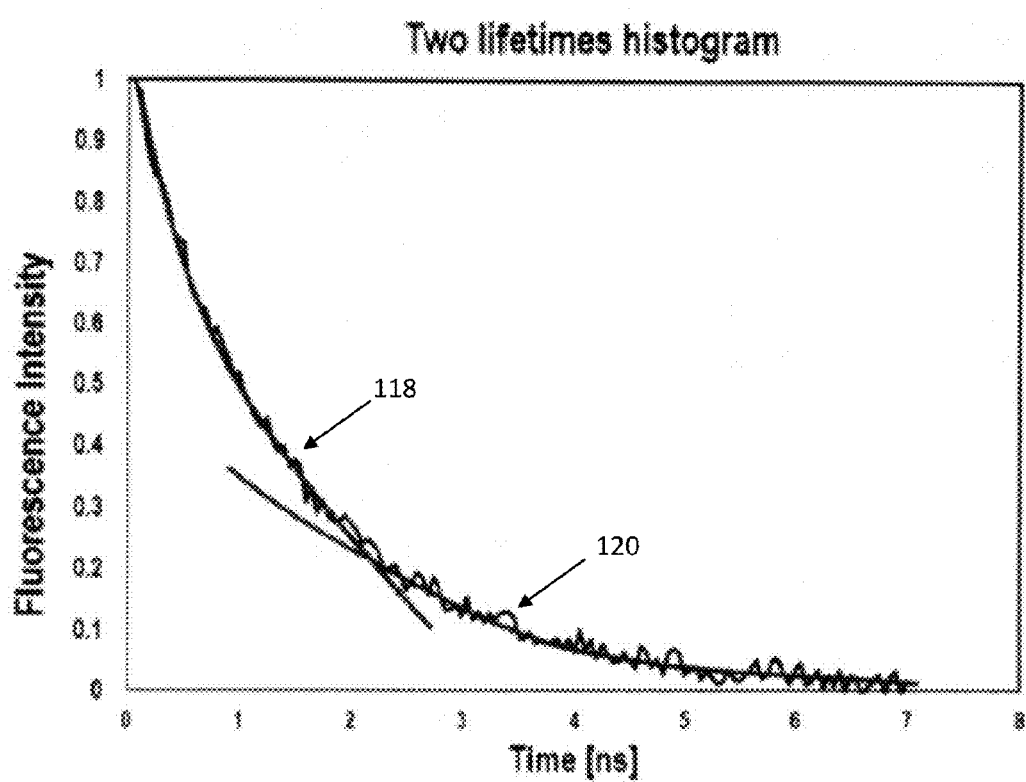
FIG. 1H shows a lifetime histogram measured for a population of fluorescent molecules having two different lifetimes fitted against two different exponential curves.

Reference is now made to FIG. 1G, which illustrates a lifetime histogram for a fluorescent molecule. Typically, a fluorescent sample is illuminated with a very short laser pulse, such as having a pulse duration in the range of 1-1000 picoseconds, and the resultant fluorescence emission may be measured at different time intervals following the pulse. The emitted photons may be collected and counted over each time interval, and plotted as a histogram which is fitted against an exponential curve, $(t)=I_0\exp[-t/\tau_F]$ where $\tau_F$ is the fluorescence life-time and $I_0$ is the maximal intensity that is emitted over a very short time interval.

Techniques for measuring fluorescent lifetimes using a microscope include gating, time correlated single photon counting (TCSPC), and phase modulation. Gating and TCSPC typically use a pulsed laser with a repetition rate that can be as high as 100 Megahertz (MHz) and provide the fluorescent light intensity, and an emitted photon count, respectively, over time. The gating technique typically uses a high time-resolution electronic counter to synchronize a detector with the illumination pulse. The electronic counter may be synchronized with an electronic clock that can measure time differences ranging from as few as 0.5 ps to several seconds. The electronic counter begins counting time from moment the sample is illuminated with the laser pulse. After a variable, predetermined time interval, such as 100 picoseconds (ps), the detector is signaled to begin counting photons emitted by the illuminated sample for a preset time window, such as 10 ps. This process may be repeated for varying time intervals from when the laser pulse is emitted. Fluorescent photon emission may thus be counted starting from as soon as 100 ps to several nanoseconds (ns) after the laser pulse illuminated the sample, allowing the exponential decay curve of FIG. 1G to be plotted. TCSPC provides similar information by measuring the time duration between emitting the laser pulse that illuminates the fluorescent sample, and detecting the first fluorescently emitted photon by the detector. This procedure may be repeated multiple times to collect sufficient data and create the lifetime histogram of FIG. 1G.

Phase modulation operates somewhat differently. The illumination laser is modulated so that its intensity has a modulating cosine-like function, and the sample is illuminating accordingly. A detector that modulates its response function with a similar cosine function to synchronize the detection with the illumination is used to detect the light emitted by the illuminated sample. The detector is controllably synchronized to detect the fluorescent signal at varying phase delays between the laser intensity and detector response. The resultant intensity curve as a function of phase delay may be used to derive the fluorescent lifetime.

Any of the above-mentioned techniques may be used to collect fluorescent lifetime measurements from 1 to as many as 100 million measurements per second.

Figure 10A:
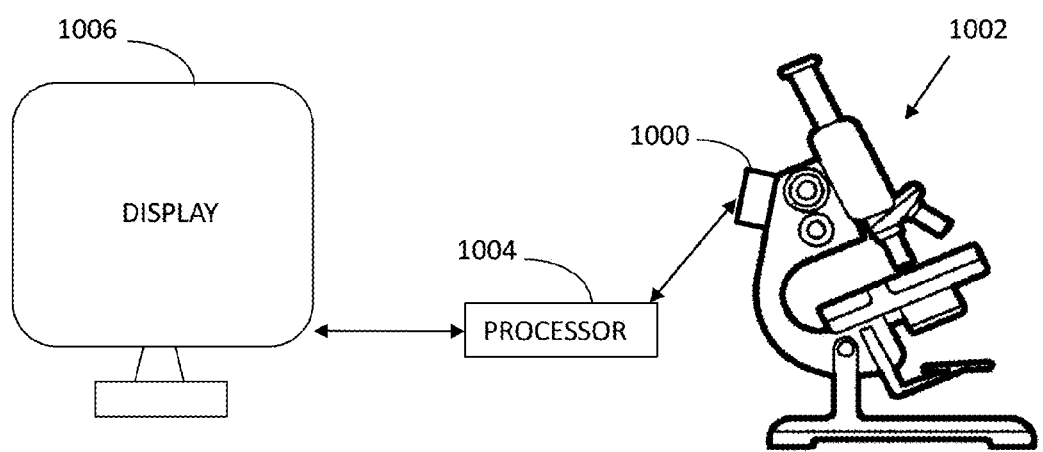
FIG. 10A illustrates a system for identifying a characteristic of a cell by analyzing multiple images of one or more labeled genetic entities, in accordance with an embodiment of the invention.
Figure 10B:
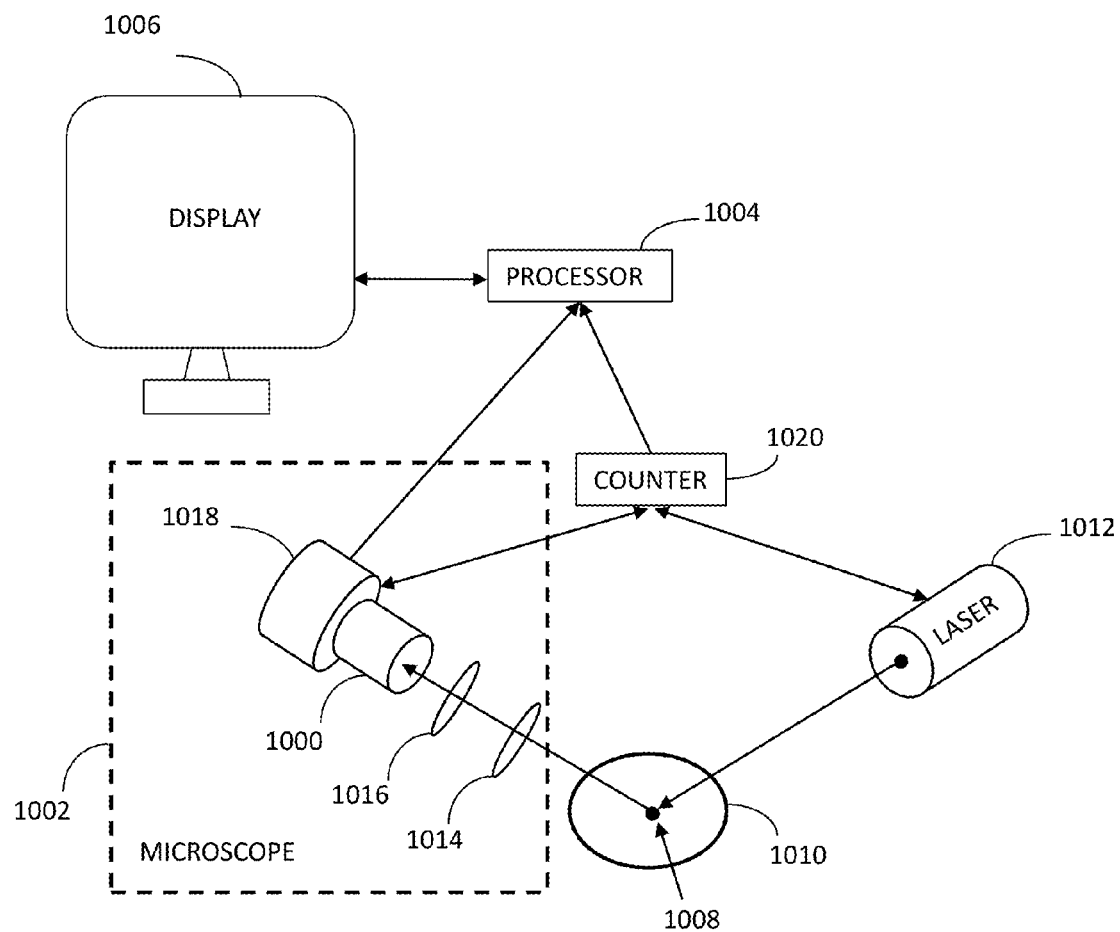
FIG. 10B illustrates a simplified conceptual illustration of a system for determining the bound to unbound ratio of proteins within a cell.

Referring to FIG. 10B, a simplified conceptual illustration of a system for determining the bound to unbound ratio of proteins within a cell is shown. It may be noted that FIG. 10B is not shown to scale. A spot 1008 on a sample 1010 is illuminated using a light source 1012, such as a pulsed diode laser source, at a wavelength corresponding to the emission spectral band of sample 1008, causing the illuminated spot on sample 1008 to fluoresce and emit a photon. The emitted light may be measured using a microscope 1002. Microscope 1002 may include an objective 1014 configured to collect the emitted light, and a mirror 1016 configured to filter the collected light. The filtered light may then be transmitted through a confocal pinhole camera 1000 and detected using a detector 1018. An electronic counter 1020 synchronizes the emission by light source 1012 with the detection by detector 1018 as described above. The intensity and fluorescent lifetime information gathered by detector 1018 and and/or counter 1020 is transmitted to a processor 1004 to determine the fluorescent light intensity and emitted photon count per predetermined time unit, and use this data to compute the ratio of bound to unbound particles, and which will be described in greater detail below. The calculated ratio may be rendered on a user interface 1006. The optical apparatus of FIG. 10B may additionally or alternatively include any of: one or more optical filters for separating the spectral range of the excitation spectral band from the emission spectral band of the fluorescent molecule; a beam splitter for separating the polarization of the excitation light and the polarization of the fluorescent light. Microscope 1002 may comprise any of: a fluorescent microscope, a transmission microscope, a dark-field microscopy apparatus, a confocal microscope, a total internal reflection microscopy apparatus, a super resolution microscopy apparatus, and a fluorescence life-time microscopy apparatus.

In one embodiment, the CP measurements may be combined with the time resolved measurements of the fluorescence signal in a method referred to as time resolved intensity photobleaching, or TRIP. By analyzing the combined data the ratio of the bound to unbound particles may be determined with higher accuracy. This may be due to the effect that the state of a molecule, i.e. bound or unbound, has on its fluorescence. For example, the fluorescent lifetime, its polarization and its polarization anisotropy lifetime may vary depending on whether the particle is bound or unbound. Various optical techniques may be used to measuring the fluorescent lifetimes and distinguish bound from free molecules.

Referring back to FIG. 1F, when a time-resolved system measures the CP intensity curve, the fluorescent lifetime of each of the molecules that takes part in the process is measured. If there is a difference in the fluorescent lifetime of the bound molecules with respect to the lifetime of the free molecules, then the lifetime that is measured for each of the bound and free populations should be different. Moreover, referring to FIG. 1H, the measured lifetime histogram of such a hybrid measurement can be analyzed by fitting against two different exponential curves, 118 and 120, and finding the ratio of intensities that each population is contributing.

Alternatively, the time-axis of the CP curve of FIG. 1F may be sectioned to smaller time-windows, such as 1 millisecond (ms) time windows. For each of these time-windows, the average fluorescent lifetime may be calculated. These average values may be accrued over a longer period to yield sufficient data to plot the histograms shown in 1I-K. For example, average values for 1 ms time windows determined over a period of 2 s will yield 2000 values, resulting in a histogram shown in FIGS. 1I-K comprising the addition of two Gaussians, each corresponding to the bound and free populations, respectively. This process may be repeated for time windows ranging from as little as one millisecond to one hundred seconds, or more.

Figure 1I:
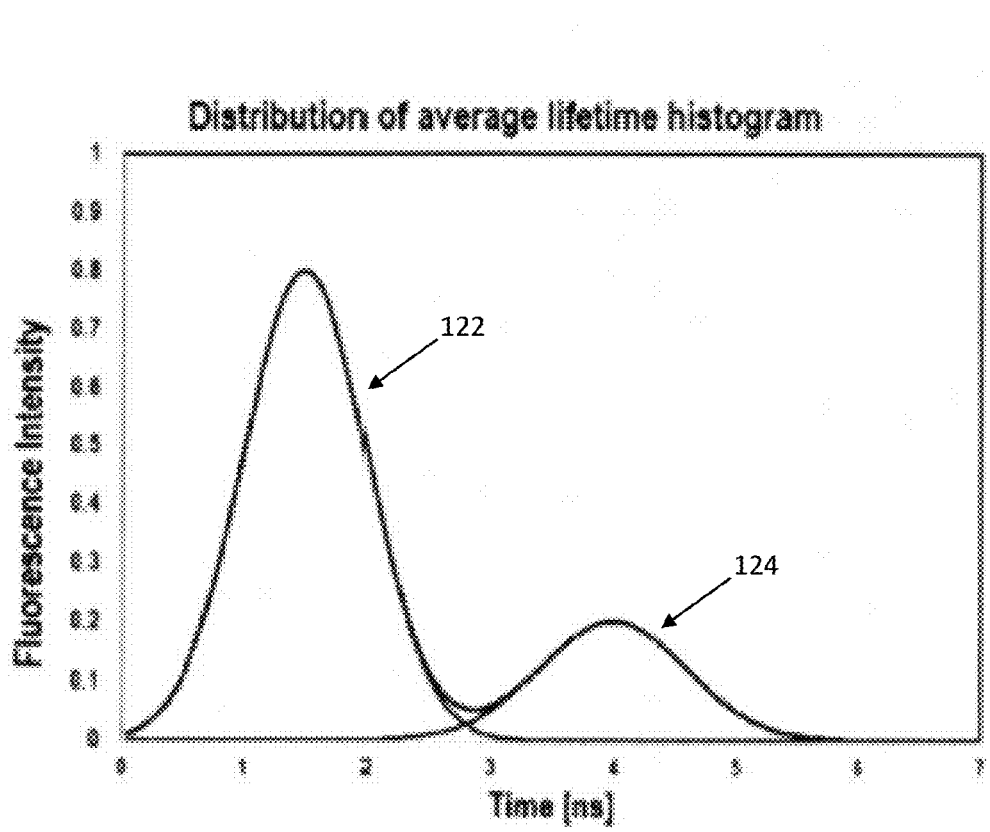
FIGS. 1I-1K show histogram distributions of average lifetimes for a population of fluorescent molecules including two subpopulations, each having a different lifetime, as measured over a 1.4 nanoseconds (ns) time-window and a 4 ns time-window, where
Figure 1J:
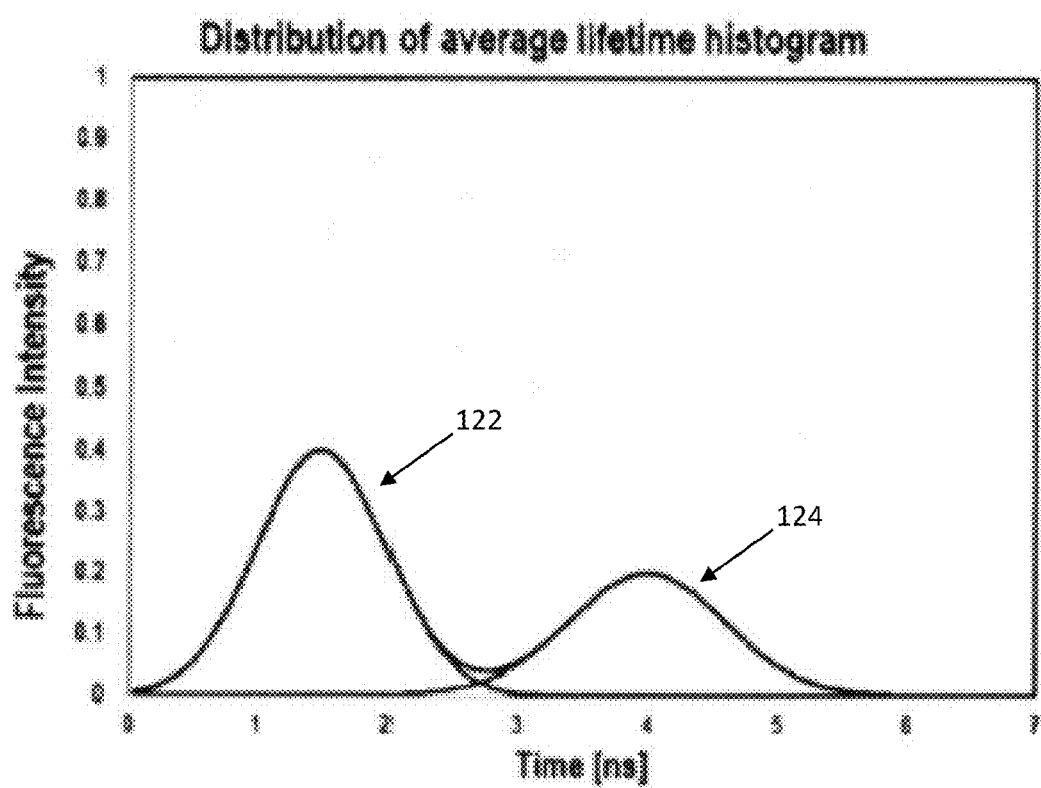
Figure 1K:
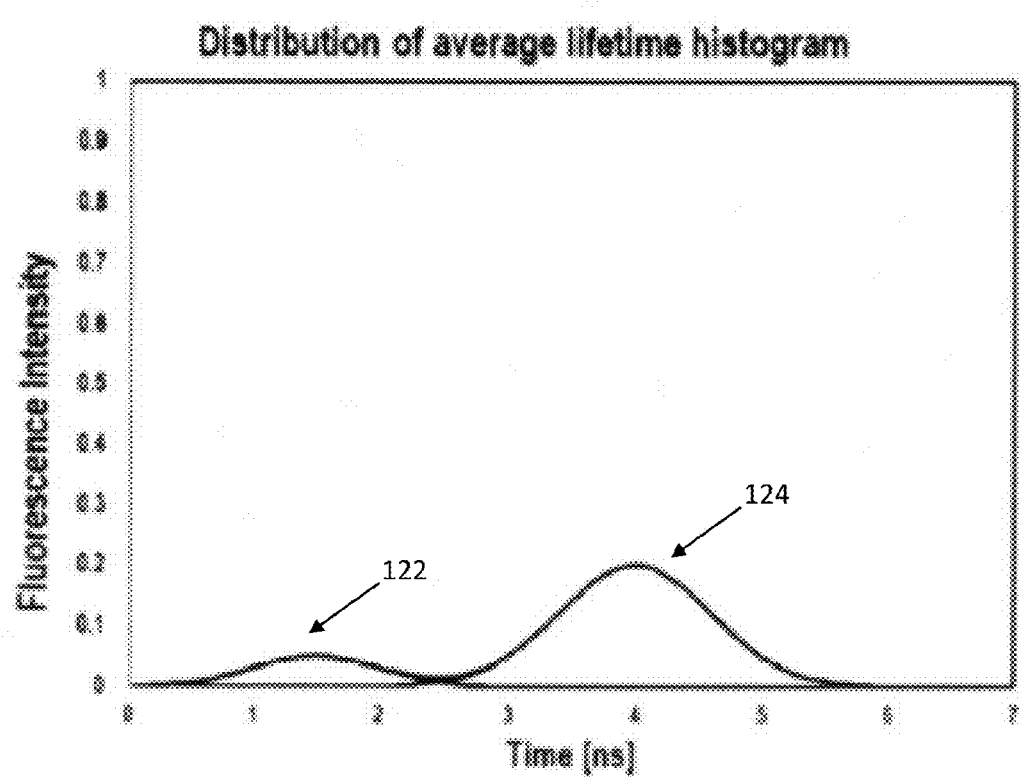

This procedure may be repeated over different time intervals along curve 116 of FIG. 1F, indicated as A, B, C. It may be noted that FIG. 1F is not shown to scale. For example, assuming that 80% of the molecules in the measured region are bound and 20% are free, at the beginning of the measurement, from the start of illuminating the sample (FIG. 1F point A), the distribution of the average fluorescent lifetimes may correspond to FIG. 1I, where Gaussian 122 represents the distribution of the lifetimes for the bound molecules, and Gaussian 124 represents the distribution of the lifetimes for the free molecules. As time passes, the fraction of the bound molecules that contributes to the diffusion will decrease. FIG. 1J shows an average fluorescent lifetime distribution for the next time period corresponding to point B, following point A of FIG. 1F, where Gaussian 122 corresponding to the bound molecules indicates substantially lower intensity levels associated with rapid decay, and Gaussian 124 corresponding to the free molecules indicates stable or slowly decaying intensity levels. After an additional time period the fraction of the bound molecules contributing to the diffusion decreases even more, in accordance with the exponential decay shown in FIG. 1F. FIG. 1K shows an average fluorescent lifetime at point C following point B of FIG. 1F, after illuminating the sample, where Gaussian 122 indicates very low intensity levels corresponding to the rapidly decaying bound molecules, and Gaussian 124 remains substantially stable, corresponding to the slowly decaying free molecules. It may be noted the time axes of FIGS. 1J-1K relate to each time interval, A, B, C.

Accordingly, the method may include the following steps:
1. Fluorescently labeling the selected protein by transfection. For example, the protein lamin A may be labeled using a green fluorescent protein by transfecting a live cell with a DNA transcript that encodes these two proteins together.
2. Selecting one or more areas of the cell for performing the measurement and illuminating the selected area with light corresponding to the protein's absorption spectrum.
3. Detecting the intensity of the fluorescent light emitted from the illuminated area with respect to time, and measuring, using a fluorescent microscope, the fluorescent lifetimes of the bound molecules to the unbound molecules.
4. Providing the data comprising the time-resolved emitted light intensity measurements and the time-resolved fluorescent lifetime measurements to a processor. This step can be repeated for the one or more selected areas over the course of the experiment.
5. Determining the CP curve and the lifetime histograms of the time resolved intensity and the fluorescent lifetime measurements using the techniques described hereinabove. The fluorescent lifetime distributions may be calculated for time windows ranging from 1 ms to 100 seconds over the course of the experiment.
6. Calculating the ratio of bound molecules to free molecules in the measured regions, such as by correlating the data from the intensity curve as a function of time (FIG. 1F) with the lifetime histogram data collected over different time-windows, as shown in FIGS. 1I-K. Any combination of the intensity curve information and lifetime histogram data may be used to determine the ratio of free to bound molecules.
7. The calculated ratio of bound molecules to free molecules may be rendered on a user interface.

The analysis may be performed in accordance with any of: linear polarization of the excitation light, linear polarization of the emitted light, circular polarization of the excitation light, and circular polarization of the emitted light. The polarization of the excitation and the emission light may be parallel to each other, perpendicular to each other, same-oriented circular polarizations, such as both being clockwise or counter-clockwise, or circular polarization where one is clockwise and the other is counter-clockwise.

Figure 2A:
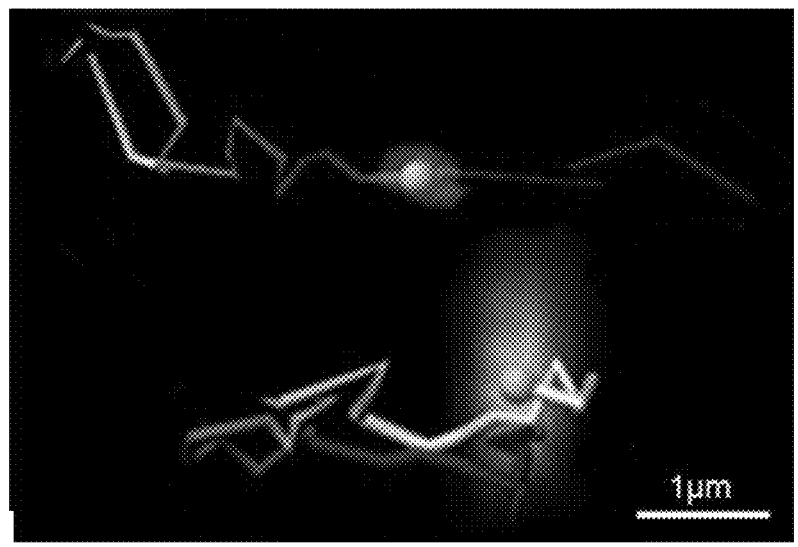
FIG. 2A shows a three-dimensional time-path of a moving particle, determined in accordance with an embodiment of the invention.
Figure 2B:
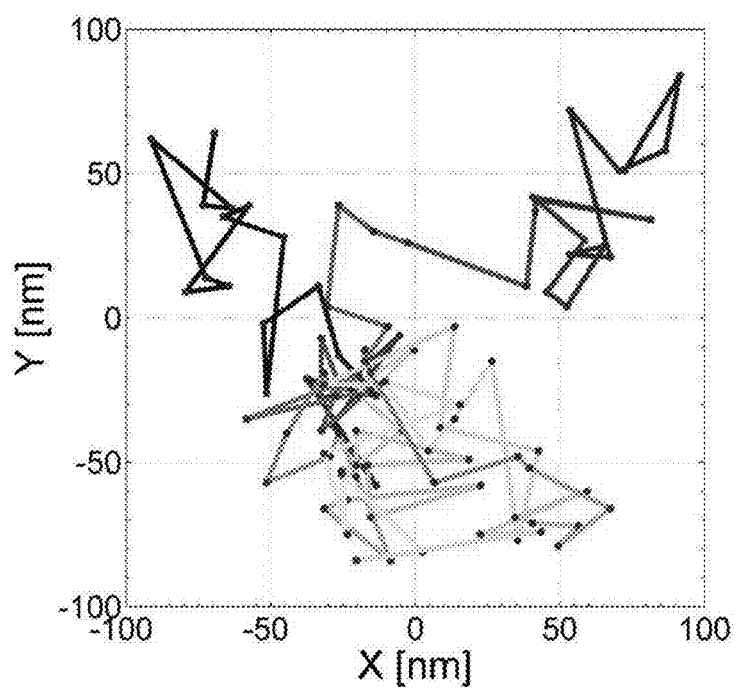
FIG. 2B shows a two-dimensional path of a moving particle, determined in accordance with an embodiment of the invention.

Reference is now made to FIGS. 2A-2B which, taken together, illustrate exemplary experimental results of applying a single particle tracking (SPT) method to measure a labeled particle's trajectory within a genomic site.

Figure 3:
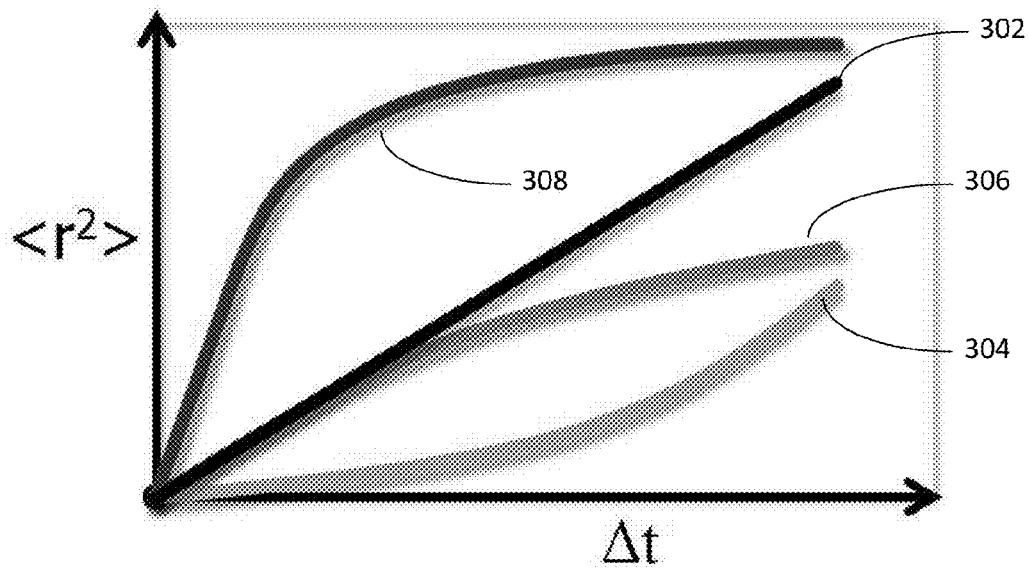
FIG. 3 illustrates various mean square displacement (MSD) curves, $<r^2>$ as a function of time.

Multiple such path trajectories r (t) may be derived for any number of particles (FIG. 2B) and analyzed to calculate a mean square displacement with respect to time (FIG. 3). The MSD measures the average distance that is travelled by the particles at a given time t. By repeating the calculation for different times, the MSD curve is found. The MSD may be applied to characterize the type of diffusion of labeled subcellular particles to determine a cell characteristic, such as the presence of an indicative protein.

Optical microscopy with high magnification may be used for capturing SPT data of particles labeled with a fluorescent dye within a live cell. A charged coupled device (CCD) camera may be used to capture two dimensional images, and confocal microscopy may be used to capture three dimensional images, such as described in Bronshtein Berger, I., E. Kepten, and Y. Garini, *Single particle tracking for studying the dynamic properties of genomic regions in live cells*, in *Imaging gene expression Methods and Protocols*, Y. Shav-Tal, Editor. 2013, Springer.

FIG. 2A shows the three-dimensional time-path of a moving particle determined from data captured using the confocal microscope, and FIG. 2B shows a similar two-dimensional path that is analyzed by using the CCD and the shading of the path indicates time along the path. This time-path may be analyzed to identify one or more dynamic, motile properties of the measured particle.

For a 2-dimensional path, the x- and y-coordinates of a tracked particle may be determined by applying an image analysis algorithm, such as by fitting a two dimensional (2D) Gaussian function to the fluorescence intensity profile captured in an image of the particle. If the fluorescent spot is bright enough and has a high signal to noise ratio, the center position may be determined to within ~10 nm precision, such as described in Yildiz, A., et al., *Myosin V walks hand-over-hand: single fluorophore imaging with 1.5-nm localization*, Science, 2003. 300: p. 2061-2066. It may be noted that precision in this case should not be confused with the spatial resolution limit, which is in the order of 200 nm due to optical diffraction limitations.

Alternatively, for a three dimensional (3D) path, the 3D position of a particle at each point in time may be determined by applying an appropriate 3D imaging method, such as via confocal microscopy, and the trajectory of a moving particle, expressed as r(t)=[x(t), y(t), z(t)], may be used for further analysis. It is also possible to extract the three dimensional path and use only two dimensional (2D) projection of the 3D path on the plane by taking for example only r(t)=[x(t), y(t)].

In an embodiment, a quantitative SPT analysis of one or more time-lapse image sequences may be performed using an image analysis software package, such as the Imaris (Bitplane) or Matlab, to determine one or more coordinates of labeled genomic loci. The images may be segmented to find the center of gravity for each identified spot, and may be repeated for multiple time-lapse images to determine a time-path for each telomere. The telomere fluorescence spots may typically be easily discernible, yielding well defined time-paths, and any missing points along the time-path of a telomere may be ignored from the analysis.

The SPT analysis may include the following steps:

i) The time-lapsed images may be analyzed in order to extract the position of the labeled particles (e.g. telomere) in the images, ii) The time-path coordinates for of the labeled particles may be used for calculating the MSD, iii) The MSDs that are calculated for multiple particles may be used for calculating an average MSD, and iv) The average MSD may be characterized from the equation type.

A more detailed description of the above-listed steps is now given.

i) In the first step, the position-coordinates of the particles in each image of the measured sequence of images may be extracted, and may be expressed as r(t)=[x(t), y(t), z(t)], where r may represent the position described in 3D coordinates, or alternatively, in 2D coordinates. An intensity threshold value may be selected for the images. Pixels that have an intensity value that is lower than the threshold value may be ignored, and the pixels having an intensity value above the threshold may be used for the analysis, such as by organizing those pixels into clusters, or 'spots'. The center of each spot may be identified using any suitable method. For example, the center may correspond to a center of mass, and values for $(x_c, y_c, z_c)$ may be calculated using the following equation:

$$x_C = \frac{\sum_j I_j \cdot x_j}{\sum_j I_j}$$

where the sum includes all the pixels j that belong to one spot, and where $I_j$ is the intensity value for pixel j. Values for $y_c$ and $z_c$ may be similarly determined.

In another embodiment, the intensity function of each spot may be fitted to a 3D Gaussian function describing the spot intensity, as follows:

$$I(x, y, z) = C \cdot \exp\left[-\frac{(x_j - x_C)^2}{2\sigma_X} - \frac{(y_j - y_C)^2}{2\sigma_Y} - \frac{(z_j - z_C)^2}{2\sigma_Z}\right]$$

where any suitable optimization algorithm may be used for finding $(x_c, y_c, z_c)$. Alternatively, any of the above methods may be applied in 2D. Such a procedure can be performed for example by the Imaris image analysis software package (BitPlane Company) or ImageJ or by writing the code in Matlab.

ii) The above procedure may be repeated for multiple spots identified in the captured image. For each image, the coordinates of the same spot may be listed over time as: $r_1(t_1), r_1(t_2), \ldots r_1(t_n)$ where i is the index of each particle, and $t_1 \ldots t_n$ are the times at which the n images where measured. In this manner, the positions of the spots over time may be described as a sequence of 3D or 2D coordinate-sets over time. This time-based sequence may be used for subsequent analysis.

In addition, the time coordinates for each telomere may be used to eliminate rotational and/or translational movement attributed to the nucleus. Correction for nucleus drift and rotation may be applied in accordance with the distribution of the telomeres that are measured for each image. The center of gravity of the telomeres may be calculated for every recorded point in time, and a movement of each specific telomere in an image may be calculated with respect to the motion of the center of gravity. A corrective factor may be added to eliminate the effect of the motion of the nucleus on the telomeres. Correction due to rotation of the nucleus may be performed by calculating the rotation of the nucleus around the whole image center of gravity and applying a suitable counter-rotation.

(iii) Multiple path trajectories derived from the SPT data thus measured may be applied to calculate the space spanned by the labeled particles as a function of time to determine their diffusion characteristics. Alternatively, the multiple path trajectories derived from the captured images by be used to calculate a space scanned by the labeled particles. These multiple path trajectories may be applied to calculate a mean square distance (MSD) function which may be used to analyze and determine the diffusion characteristics of the labeled particles. Since the average distance of a particle from the origin does not change with time, the MSD, $\langle r^2(t) \rangle$, of a particle may be used to determine the quadratic length of a particle's excursions from the origin.

Normal subcellular particle diffusion, such as Brownian motion, may exhibit a linear increase with respect to time, and may be described as: $r^2(t) = 2dDt$, with d being the trajectory dimension, and D being the diffusion constant. Conversely, if a particle is slowed down by the surrounding environment, an anomalous subdiffusion may be observed, and may be described by $\overline{r^2(t)} = A \cdot t^\alpha$ where A is a constant and is a positive number, $\alpha < 1$.

The MSD may be calculated as an average distance travelled over time t by an ensemble of N particles, and may be described by:

$$\langle r^2(t) \rangle = \frac{1}{N} \sum_{i=1}^{N} [r_i(t) - r_i(0)]^2 \qquad \text{(Eq. 1)}$$

In one embodiment, a time averaged MSD may be calculated over a path for a single particle over time T, by calculating the average square distance for all steps with time difference t, where a bar indicates averaging over time:

$$\overline{r^2(t)} = \frac{1}{T-t} \sum_{\tau=0}^{T-t} [r(\tau + t) - r(\tau)]^2 \qquad \text{(Eq. 2)}$$

This time averaged MSD may be analyzed to identify one or more properties of the labeled particles, such as their diffusion characteristics, to determine a property of the cell, as follows:

In simple Brownian motion, both the ensemble averaged MSD and the time averaged MSD measurements may follow a linear dependence with time t:

$$\langle r^2(t) \rangle = 2nDt \quad \text{(Eq. 3)}$$

where n represents the spatial dimension, and where D represents the diffusion coefficient. For example, for a 2D measurement n=2. A linear MSD function, such as described by equation 3, may be correspond to a linear diffusion process and may be designated as 'normal diffusion'.

In cases where the MSD function is not linear with respect to time t, the diffusion may be designated 'anomalous'. When MSD grows as a power of time, it may be described as follows:

$$\langle r^2(t) \rangle = At^\alpha \quad \text{(Eq. 4)}$$

When $0 < \alpha < 1$, the particles move slower than normal diffusing particles and have a higher probability of interaction with nearby targets in a process known as 'subdiffusion'. This may indicate that the particle is diffusing in a non-homogeneous space. Conversely, when $1 < \alpha$, the particles may move faster than for normal diffusion, in a process known as 'super-diffusion'.

Thus, analysis of anomalous diffusion of particles may be applied to determine a characteristic of a cell by quantifying the crowdedness of the cytoplasm at the molecular scale or to identify molecular interactions, such as described in Bronstein, I., et al., *Transient anomalous diffusion of telomeres in the nucleus of mammalian cells*, Physical Review Letters, 2009. 103: p. 018102. Anomalous diffusion pattern may correspond to a healthy cell, whereas normal diffusion pattern may correspond to a deficiency in a protein that is critical to the cell's function. In this manner, the motile property manifested as a diffusion characteristic may identify an expression or activity of a nuclear protein in the cell.

Reference is now made to FIG. 3 which illustrates various mean square displacement curves (MSD), <r²> as a function of time. The shape of the MSD curve, such as expressed by the derivative, or slope of the curve with respect to time, may be applied to determine a diffusion characteristic of the nuclear protein. Curve 302 with a linear shape may correspond to a normal diffusion pattern, curve 304 with an exponentially increasing shape may correspond to an anomalous super diffusion pattern, curve 306 with a logarithmic shape, may correspond to an anomalous sub-diffusion pattern, and curve 308, beginning with a linear shape that levels off after a given time duration may correspond to a normal diffusion pattern within a restricted volume of space. These curve shapes may comprise a set of rules that may be applied to identify the diffusion characteristic for a given particle. A more detailed explanation of how these rules may be applied is given below with respect to FIGS. 6A-6B.

An MSD graph may be derived using the method disclosed herein for one or more labeled particles, and may be compared to such a set of predefined curves that are each associated with a diffusion characteristic. The diffusion pattern associated with the best fitting curve may be identified with the labeled particles, and compared to a predefined shape associated with a diffusion type, such as the shapes illustrated in FIG. 3, to identify the diffusion type of the labeled particles, thereby determining a characteristic of the cell, such as the presence or lack of an indicative protein.

In another embodiment, a convex hull function may be applied to determine the area, or volume that is scanned, or spanned by the particle, or telomere, for the duration of the experiment. A convex hull function is known to one skilled in the art as well as from Franco Preparata & S. J. Hong, "Convex Hulls of Finite Sets of Points in Two and Three Dimensions", Communications of the ACM 20, 87-93 (1977). Given the coordinates of the particle over a timeframe, such as obtained above in step (ii), a flexible surface such as a 'plastic bag' may be spread to cover the coordinates, and the amount of 'plastic bag' required to cover the coordinates, such the area or volume of the plastic bag, may provide a measurement of the scanned area or volume, accordingly. This area or volume as a function of time may provide a measure of the dynamics of the particle, and may be compared across different cells or treatment types, and analyzed as described above. Alternatively, a predefined threshold may be compared to this measurement to distinguish between normal and anomalous cells.

Figure 4:
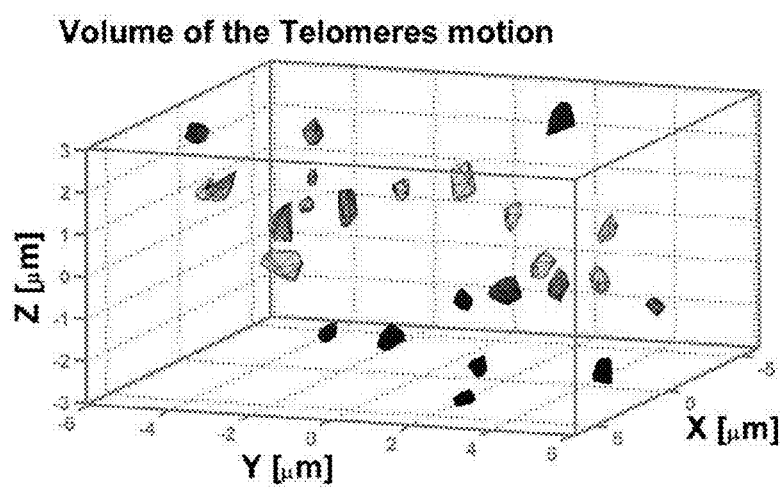
FIG. 4 illustrates exemplary experimental results of a method for calculating the volume that is spanned by diffusing particles within the nucleus of a cell within a given timeframe.

Reference is now made to FIG. 4, which illustrates exemplary experimental results of a method for calculating the volume scanned by diffusing particles within the nucleus of a cell over a given timeframe. The volume spanned by each diffusing marked particle may be calculated, in either two or three dimensions, over the predefined time period, and the average volume spanned by all the marked particles may be computed. In the example of FIG. 4, the diffusion volume was calculated in three dimensions over a time period of 20 minutes, and a convex hull algorithm was applied to determine the spanned space. This average spanned space value may be applied to determine another dynamic property of the dynamics of the marked particles. For example, a small average space may indicate 'slow' diffusion associated with bound particles, whereas a large average space may indicate 'fast' diffusion associated with unbound particles. It may be noted that in this context, the terms 'slow' and 'fast' are to be understood as some of multiple qualitative descriptive parameters of the particles dynamics, and that the described volume is related to the diffusion in a rather complex manner.

In an embodiment, time averaged MSD may be calculated for a genome locus as the average squared displacement realized between any two time points and separated by a time interval τ, where τ=n·δt, δt is the time interval between any two measurements, and n is an integer. The average displacement may be computed over the measured time duration, and may be expressed as:

$$\langle r^2(\tau) \rangle = \frac{1}{N-n} \sum_{m=1}^{N-n} [\vec{r}((m-1)\delta t + \tau) - \vec{r}((m-1)\delta t)]^2 \quad \text{(Eq. 5)}$$

Here, $\vec{r}$ represent a two or three dimensional position vector of the particle at each time point and N represent the total number of time points measured (total number of images), and the sum runs over m. In an embodiment, analysis of the measured data may be performed only on the planar X-Y plain motion since the Z axis (optical axis) may have higher measurement errors, and can be neglected.

Figure 5:
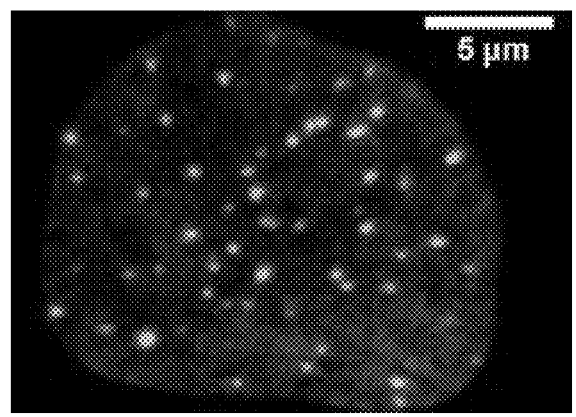
FIG. 5 illustrates exemplary results of a method for capturing images of particles labeled with green fluorescent proteins (GFP) within the nucleus of a live cell.

Reference is now made to FIG. 5, which illustrates exemplary results of a method for capturing images of particles labeled with green fluorescent proteins (GFP) within the nucleus of a live cell. It may be noted that other fluorescent proteins may be used to mark the particles. Thus, it may be possible to label many different proteins and other such structures in a living cell. In an embodiment, a transfection method, as described in Day, R. N. and M. W. Davidson, *The fluorescent protein palette: tools for cellular imaging*, Chemical Society Reviews, 2009. 38: p. 2887-2921, may be applied to label subcellular particles. The measurement may be obtained at an image rate of 100 Hz (every 10 milliseconds), or at a longer time-gap (lower rate) and the sample may be measured for a total long or short times. In one embodiment, if a high rate is used, such as 100 Hz, data may be gathered over a timeframe ranging from about 10-30 seconds, to collect approximately 100 images or more. If a slower rate is used, such as by measuring an image every 20 seconds, the measurement may continue for an hour where 180 images will be collected. It is also possible to repeat the measurement few times, once at a high frame rate and then again at a lower frame rate. By combining the data, it is possible to calculate values such as the MSD for a broader time gap.

For example, telomeres or centromeres in the nucleus of eukaryotic cells may be labeled. Mouse embryonic fibroblasts lacking lamin A/C (Lmna$^{-/-}$) and their wild type (Lmna$^{+/+}$) MEFs may be maintained in a medium such as Dulbecco's low glucose modified Eagles medium containing 10% of bovine serum, 1% of penicillin and streptomycin antibiotics. Both cell types may be transfected with GFP-TRF2 plasmid, to allow observation of the telomeres with fluorescence microscopy.

(iv) Having obtained MSD, or alternatively, MSV values with respect to time using any of the methods described above, the MSD or MSV may be fit to one or more predefined curves, such as described in Equation 6 below, to determine a characteristic curve, or equation type and characterized according to the equation with the best fit.

Figure 6A:
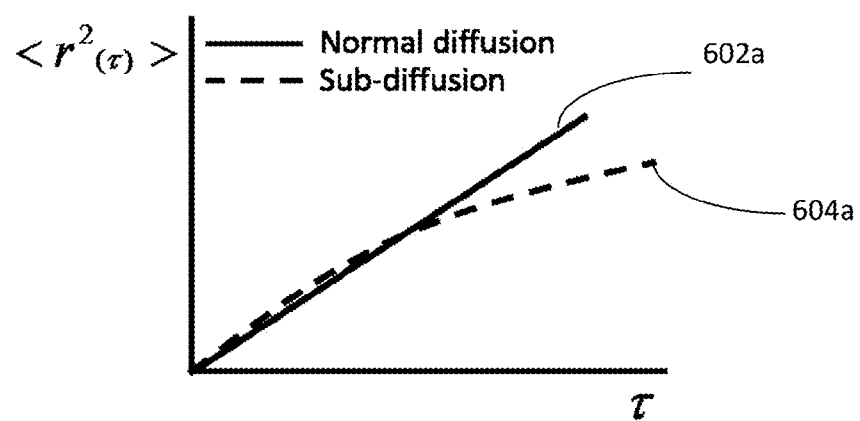
FIGS. 6A-6B, taken together, illustrate normal diffusion and sub-diffusion MSD patterns, in accordance with an embodiment described in two different axes system.
Figure 6B:
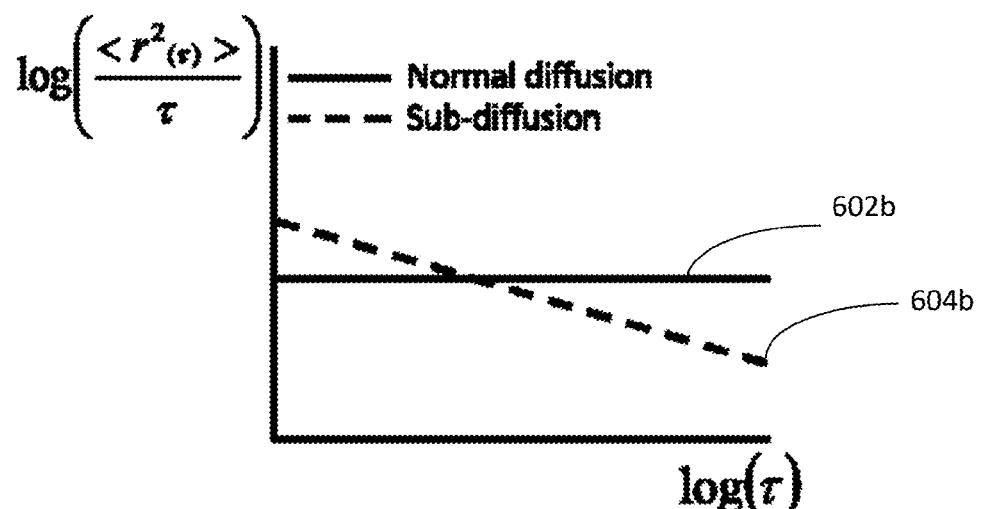

Reference is now made to FIGS. 6A-6B which illustrate normal diffusion and sub-diffusion MSD patterns, in accordance with an embodiment. Referring to FIG. 6A, MSD values are shown plotted with respect to time. MSD curve 602a, shown with a solid line, increases at a constant rate corresponding to normal diffusion behavior, and for a diffusion in a plane, may be represented by $<r^2(\tau)>=4D\tau$, where D is the diffusion coefficient. Conversely, curve 604a, shown with a dashed line, decays exponentially with time corresponding to sub-diffusion behavior.

Referring to FIG. 6B, the same MSD values are shown plotted with respect to time on a log-log scale, but here the plotted MSD is divided by time. Here, normal diffusion translates to a horizontal line with a zero slope, shown as curve 602b with a solid line, anomalous sub-diffusion translates to a negative-slope curve, shown as curve 604b with a dashed line, and anomalous super-diffusion may have a positive slope (not shown). The slope of each curve can be used to extract the anomalous coefficient α as follows:

$$<r^2> = D_\alpha \tau^\alpha \quad \text{(Eq. 6)}$$

$$\frac{<r^2>}{\tau} = D_\alpha \tau^{\alpha-1}$$

$$\log \frac{<r^2>}{\tau} = (\alpha - 1)\log\tau + \log D_\alpha$$

Accordingly, different values for α may characterize the diffusion type, and the underlying cell characteristic. For example, α=0 may correspond to normal diffusion, α<0 may correspond to anomalous sub-diffusion, and α>0 may correspond to anomalous super-diffusion.

In an embodiment, it may be possible to improve the accuracy of the MSD curves applying the method described in Kepten, E., I. Bronshtein, and Y. Garini, *Improved Estimation of Anomalous Diffusion Exponents in Single-Particle Tracking Experiments. Physical Review E,* 2013. 87: p. 052713.

In another embodiment, data gathered from the continuous photo-bleaching (CP) technique may be similarly analyzed either alone or in combination with any of the methods described above, such as STP, MSD, and/or MSV, to identify a motile property of a labeled protein, and determine a cell characteristic associated with that motile property.

Experimental Results

Figure 7A:
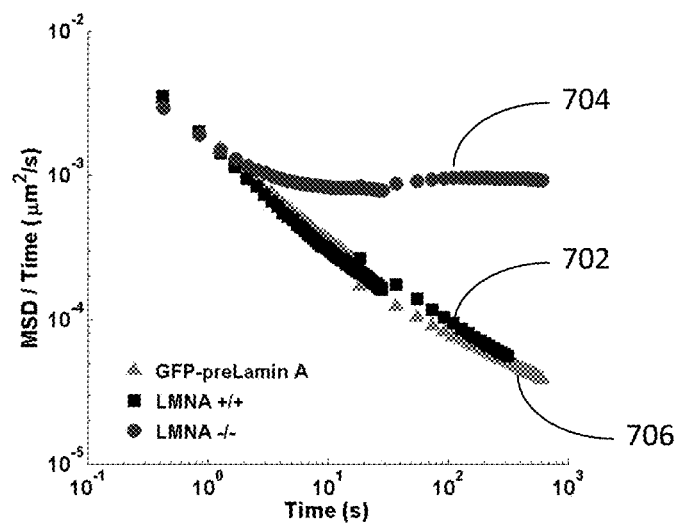
FIGS. 7A-7B, taken together, illustrate experimental results of calculated MSD values for wild type cells and cells with depleted lamin A, in accordance with an embodiment of the invention.
Figure 7B:
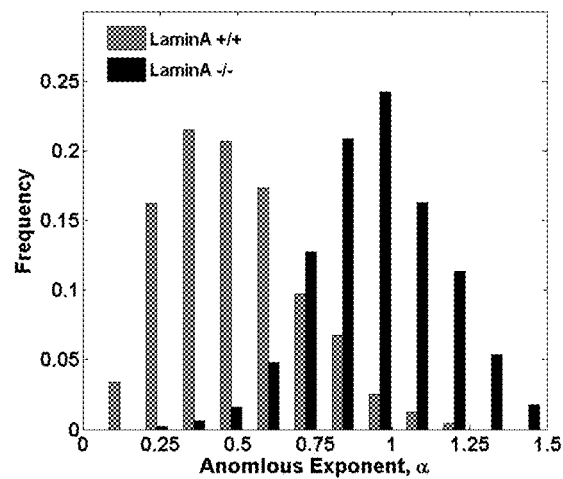

Reference is now made to FIGS. 7A-7B which, taken together, illustrate experimental results of calculated MSD values for wild type cells and cells with depleted lamin A, using the system and methods described herein.

Referring to FIG. 7A, curve 702 shows the MSDs calculated for telomeres in mouse embryonic fibroblasts labeled with GFP-TRF2 for Lmna+/+ cells, with respect to time. Upon analyzing curve 702, the diffusion was determined to be anomalous, with a value for α=0.43±0.15. Slow anomalous sub-diffusion can thus be regarded as a typical diffusion of genomic sites in the nucleus, exhibiting slow and localized motion. In contrast, curve 704 shows a normal diffusion of telomeres for Lmna-/- MEFs for τ>7 with α=1±0.2. Referring to FIG. 7B, a transition of the diffusion pattern from anomalous to normal may be demonstrated in the histograms of individual telomere exponents α, where values corresponding to individual telomeres in Lmna+/+ are shown as white bars, and values corresponding to Lmna-/- cells, shown as black bars.

Referring back to FIG. 7A, curve 706 shows an expression of transfected GFP-pre-lamin A in Lmna-/- MEFs restored the anomalous nature of telomere diffusion, with α=0.6±0.1.

Reference is now made to FIG. 8A which shows experimental results of an area scanned by 350 randomly selected telomeres during 15 minutes as calculated using a convex hull algorithm. FIG. 8A illustrates measured results for 15 Lmna+/+ cells. A similar figure (not shown) could show results for 15 Lmna-/- cells, where scanned areas are shaded according to the same logarithmic scale. In this experiment, Lamin A depletion led to faster genome dynamics as well as a larger scanned nuclear areas, is clearly demonstrated by the plotted telomere and centromere movement areas. FIG. 8B shows average scanned volumes by telomeres over 15 min in Lmna+/+, Lmna-/- cells and in these same cells transfected with GFP-pre-lamin A. Without lamin A, the volume of telomere motion greatly increases, thus these plots may be used to determine presence or concentration of lamin A, the lack of which may be related to different diseases that are collectively named laminopathis.

Figure 9:
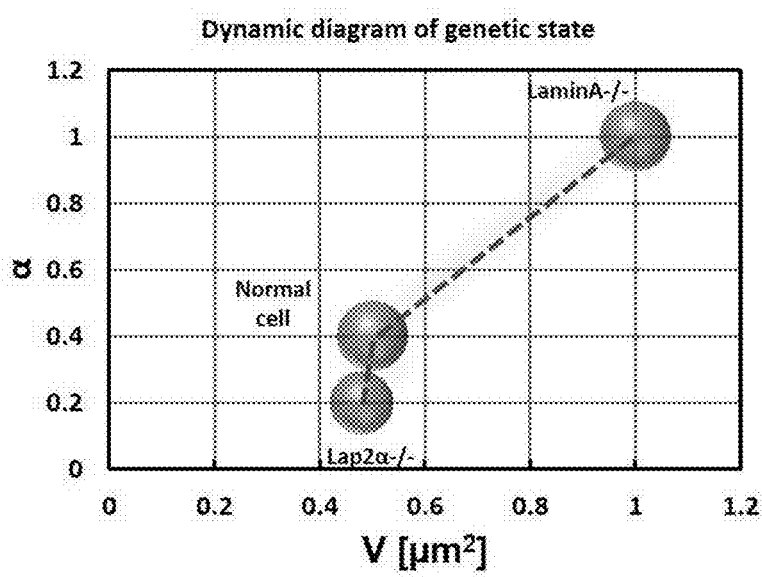
FIG. 9 illustrates an experimentally measured range of distribution for $Lmna^{+/+}$ cells, $Lmna^{-/-}$ cells and $Lap2\alpha^{-/-}$ cells, in accordance with an embodiment of the invention.

Reference is now made to FIG. 9 which illustrates an experimentally measured range of distribution of dynamic parameters for Lmna$^{+/+}$ cells, Lmna$^{-/-}$ cells and Lap2α$^{-/-}$ cells, in accordance with an embodiment of the invention. Each cell-type may be related to a different regime of the dynamic plot.

The value of the diffusion exponent, a, as given in Equation 4, may provide information regarding the diffusion type. As describe above, values of α<1 may be related to normal cells, while values of α=1 may be related to cells with a protein deficiency. In addition, the volume scanned by each particle, and the average of many particles, also reflects the dynamics that is affected by certain proteins. Therefore, by plotting a dynamic diagram of both parameters, important information is observed and can be used for identifying the structural status of cells in different expression levels and diseases. Such a plot is shown in FIG. 9. Different areas in this plot are related to different cell types.

Reference is now made to FIG. 10A which illustrates a system for determining a cell characteristic from one or more images of labeled genetic entities in accordance with the methods and apparatus described above.

An image capturing apparatus, such as a camera 1000 coupled with a microscope 1002 comprising any of the CCD or confocal microscope apparatus described herein, may capture multiple images of multiple labeled genetic entities. The images may be captured using any of the following techniques: fluorescent microscopy, transmission microscopy, dark-field microscopy, confocal microscopy, total internal reflection fluorescence microscopy, phase microscopy, polarization microscopy, super resolution microscopy (STED, PALM, STORM, structured illumination microscopy), fluorescence life-time microscopy, or application of fluorescent proteins. Images of living cells may be obtained by placing the cells in an incubator, such as a Tokai incubator, that is maintained at 37 degrees C. with a 5% $CO_2$ level, and placed on an inverted fluorescence microscope, such as Olympus IX-81. The microscope may be coupled to a confocal setup, such as an FV-1000 confocal setup (Olympus). Imaging may be performed with a UPLSAPO 60× objective, with NA=1.35.

The captured images may be received at a processor 1004 via a wired or wireless communications system and analyzed in accordance with the methods described herein to determining a cell characteristic. Processor 1004 may perform any of the calculations described hereinabove and render the results on a display 1006.

For example, processor 1004 may calculate an MSD function with respect to time by analyzing multiple such images of labeled genetic entities. The analysis may include: calculating the MSD at different time-ranges; fitting the MSD to a power-law function over at least one time-range to extract a power parameter; calculating a range, area or volume scanned by the labeled entities over the given time-range; calculating and extracting a coefficient preceding the power-law function; calculating one or more statistics of the parameters calculated above to determine any of: a mean, median, mode, standard deviation, range, percentile, skewness, kurtosis, moments; and render a histogram of the calculated statistics on display 1006.

One or more rules, such as any of the rules described above, may be applied to the MSD function to identify the diffusion type and determine the cell characteristic. The rules may include: a shape of the MSD curve, the type of labeled genetic entities captured in the images, a derivative of the MSD curve, the curve shape along the time duration of the MSD curve, the power parameter corresponding to the power-law function fitted to the MSD curve, to name a few.

Additionally, processor 1004 may compute the ratios of free to bound molecules using the techniques described above with respect to CP.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is to be understood that the following claims are to cover all generic and specific features of the invention described herein, and all statements of the scope of the invention which, as a matter of language, might be said to fall there between.

The present invention may be a system, a method, and/or a computer program product. The computer program product may include a computer readable storage medium (or media) having computer readable program instructions thereon for causing a processor to carry out aspects of the present invention.

The computer readable storage medium can be a non-transitory, tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention may be described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for determining the ratio of bound to unbound molecules in a cell, comprising:
    obtaining, from a selected area of a cell, data comprising time-resolved emitted light intensity measurements and time-resolved fluorescent lifetime measurements of fluorescently labeled bound molecules and fluorescently labeled unbound molecules;
    determining from the obtained data 1) a continuous photobleaching (CP) curve and 2) fluorescent lifetime histograms for each of the time-resolved emitted light intensity measurements and fluorescent lifetime measurements; and
    calculating a ratio of the fluorescently labeled bound molecules to the fluorescently labeled unbound molecules in the selected regions using the CP curve and the fluorescent lifetime histograms.

2. The method of claim 1, further comprising:
    fluorescently labeling the molecules;
    selecting the area;
    illuminating the selected area with light corresponding to the molecules' absorption spectrum;
    detecting the light intensity emitted from the illuminated area; and
    measuring the fluorescent lifetimes of the bound molecules to the unbound molecules.

3. The method of claim 2, further comprising synchronizing the illumination and detection steps, wherein synchronizing comprises applying any of a gating technique, time correlated single photon counting technique, and phase modulation technique.

4. The method of claim 1, wherein calculating further comprises correlating the CP curve with the fluorescent lifetime histograms over time.

5. The method of claim 1, wherein illuminating comprises emitting a laser pulse having a duration ranging between 1 and 1000 picoseconds.

6. The method of claim 1, wherein the molecules are fluorescently labeled using fluorescing molecules selected from the group consisting of molecular probes, fluorescent proteins, quantum dots, metallic particles, and a dye measurable via bright field microscopy.

7. The method of claim 2, wherein the measuring step comprises determining any of the fluorescent light intensity and an emitted photon count per a predetermined time unit.

8. The method of claim 7, further comprising repeating performing said obtaining, determining and calculating steps for a time window ranging from one millisecond to one hundred seconds.

9. The method of claim 2 wherein measuring the light intensity comprises optically filtering the spectral range of the excitation spectral band from the emission spectral band of the emitted light.

* * * * *